(12) United States Patent
Michishita et al.

(10) Patent No.: US 8,105,259 B2
(45) Date of Patent: Jan. 31, 2012

(54) CATHETER

(75) Inventors: Ichiro Michishita, Yokohama (JP); Takuji Nishide, Settsu (JP)

(73) Assignee: Kaneka Corporation, Osaka (JP)

( * ) Notice: Subject to any disclaimer, the term of this patent is extended or adjusted under 35 U.S.C. 154(b) by 634 days.

(21) Appl. No.: 11/816,697

(22) PCT Filed: Feb. 21, 2006

(86) PCT No.: PCT/JP2006/303080
§ 371 (c)(1),
(2), (4) Date: Aug. 20, 2007

(87) PCT Pub. No.: WO2006/090707
PCT Pub. Date: Aug. 31, 2006

(65) Prior Publication Data
US 2009/0287135 A1    Nov. 19, 2009

(30) Foreign Application Priority Data

Feb. 22, 2005 (JP) ................................. 2005-045725
Oct. 13, 2005 (JP) ................................. 2005-298985

(51) Int. Cl.
*A61M 37/00* (2006.01)
(52) U.S. Cl. ..................... 604/4.01; 604/6.11; 604/6.16; 604/508
(58) Field of Classification Search ................. 604/4.01, 604/5.01, 5.04, 6.09, 6.11, 507, 508, 8, 9
See application file for complete search history.

(56) References Cited

U.S. PATENT DOCUMENTS 5,713,861 A * 2/1998 Vanarthos ................. 604/103.03
6,610,046 B1 * 8/2003 Usami et al. ................. 604/530

FOREIGN PATENT DOCUMENTS

| JP | 03-092170 | 4/1991 |
| JP | 04-132557 | 5/1992 |
| JP | 07-265411 | 10/1995 |
| JP | 07-303701 | 11/1995 |
| JP | 09-253214 | 9/1997 |
| JP | 11-000402 | 1/1999 |
| JP | 2000-233026 | 8/2000 |
| JP | 3103872 | 6/2004 |
| WO | WO 03/103744 A2 | 12/2003 |

OTHER PUBLICATIONS

Japanese Office Action dated Apr. 19, 2011 for Application No. 2005-298985; translation-in-part included.

* cited by examiner

*Primary Examiner* — Leslie Deak
(74) *Attorney, Agent, or Firm* — Antonelli, Terry, Stout & Kraus, LLP.

(57) ABSTRACT

The present invention provides a catheter for extraction that can efficiently extract blood flowing in coronary sinus from coronary artery through coronary vein and has the same operability as catheters used in conventional PCI. The present invention also provides a catheter for extracorporeal circulation that can lessen an introduction number of devices for blood access as little as possible and reduce further the burden to a patient, in addition to the same operability as the catheters used in the conventional PCI. The catheter for extraction is equipped with blood extracting lumen in an inside and equipped with a hub at a proximal end portion, and when a minimum sectional area to a circumferential direction of the blood extracting lumen is referred to as S1 and immersion side length is referred to as L1, an equivalent diameter D1 satisfies the formula defined by $D1=(4 \times S1)/L1$ and the equivalent diameter D1 is at 1.80 mm. The catheter for extracorporeal circulation also has blood extracting lumen extending from the distal end to the proximal end and blood return lumen extending from the proximal end of the catheter to a fixed length distal end.

2 Claims, 23 Drawing Sheets

CATHETER

CROSS-REFERENCE TO THE RELATED APPLICATION

This application is a national stage of international application No. PCT/JP2006/303080 filed Feb. 21, 2006, the entire contents of which are incorporated by reference. This application also claims benefit of priority under 35 U.S.C. §119 to Japanese Patent Application No. 2005-045725 filed Feb. 22, 2005 and Japanese Patent Application No. 2005-298985 filed Oct. 13, 2005, the entire contents of both of which are incorporated by reference.

TECHNICAL FIELD

The present invention relates to a catheter used for medical uses and more specifically relates to a catheter for extraction that temporarily extracts blood externally for removing a contrast medium locally administrated to coronary artery from blood and a catheter that can temporarily extract blood from coronary sinus externally and then can return blood internally.

BACKGROUND ART

When stenosis or occlusion occurs in vascular channels such as the blood vessel, or when the blood vessel is blocked by thrombus, angioplasty (PTA: Percutaneous Transluminal Angioplasty and PTCA: Percutaneous Transluminal Coronary Angioplasty) by which stenosis site or occlusion site is expanded with a balloon catheter and improves blood flow at angioperiphery side has been conventionally found in many operative examples in medical organizations and is general as the remedy for such diseases.

Atherectomy remedy in which atheroma is cut by transcatheter has been carried out in accordance with the progress of devices such as DCA (Directional Coronary Atherectomy) and a rotor brator. Further, there have been many stents and the like that are placed for keeping the patency state of the expanded stenosis site and occlusion site. These PTCA, Atherectomy remedy, stenting and the like are named generically as percutaneous coronary intervention (PCI). Cases with high difficulty such as the legion of left coronary main trunk (LMT) and the legion of chronic total occlusion (CTO) have been the adaptation of PCI.

The contrast medium is an indispensable drug at coronary angiography (CAG) and PCI and used widely. On the other hand, it has been known that the contrast medium has side reactions such as renal function disorder, cutaneous disorder, cardiovascular disorder, respiratory apparatus disorder and urinary organs disorder. Consequently, there has been carried out tries for suppressing the use amount of the contrast medium as little as possible by using an injector and the like.

However, angiography cycles are increased in cases with high difficulty such as the LMT legion and CTO legion and the use amount of the contrast medium is increased inevitably. Further, drug eluting stent (DES) dramatically reducing the occurrence of restenosis after the stenting has been recently developed and is resulting in high remedy effect, but it is status quo that much more contrast medium is used for the accurate grasping of legion properties such as blood vessel diameter and length and the positioning of DES for the legion at the deployment of DES.

It has been recently reported that the complication of diabetics is found in many patients carrying out PCI and the renal function disorder is a problem among the side reactions by the contrast medium. Hydration before and after PCI, the administration of N-acetylcysteine and the like and the removal of the contrast medium by dialysis after PCI have been tried for kidney failure patients in particular, in order to suppress the renal function disorder called as the contrast induced nephropathy.

Among these, it is considered that dialysis is an effective means for removing the contrast medium in the blood but there has been reported that its effect is questionable. As presented in Coronary Intervention, Vol. 2, No.4, (2003) pp 78 to 83, difference in the frequency of occurrence of the contrast induced nephropathy is not confirmed between a group (dialysis group) in which dialysis was carried out for chronic kidney failure patients after use of the contrast medium and a group (non dialysis group) in which no dialysis was carried out. Since time from the administration of the contrast medium to dialysis is long, it is suggested that the blood containing the contrast medium continues to circulate in the body and it is cause for provoking the renal function disorder. From these backgrounds, a remedy system that reduces load to the kidney by the contrast medium during PCI is required and related technology is developed.

Japanese Unexamined Patent Publication No. 7-303701 discloses a balloon catheter equipped with an expandable balloon, catheter lumen extended from a proximal portion to a distal portion and a catheter main body having the catheter lumen extending from the proximal portion to the balloon, wherein a plurality of opening hole portions penetrated in the fore-mentioned catheter lumen at the edge side from the balloon of the catheter main body are provided.

FIG. 13 shows the sectional schematic diagram of the heart. The purpose of a conventional catheter 17 for extraction is that it is arranged at the coronary sinus opening 16 through the right atrium 15 from inferior vena cava 14, blood flow from the coronary sinus opening 16 to the right atrium 15 is blocked by expanding the balloon nearly at the same time with the administration of the contrast medium to the coronary artery and the blood containing the contrast medium administrated in the coronary artery is collected from the catheter lumen. The contrast medium in the blood collected is removed by adsorption and filtration, and the load to kidney by the contrast medium can be reduced by hydrating the blood after removal in the body. However, the conventional catheter 17 for extraction had a problem below.

Firstly, it is difficult to expand the balloon at the coronary sinus opening 16 and block the blood flow to the right atrium 15. The coronary artery is connected to the arteriolae and circulated to the venulae through capillary blood vessel. The several arteriolae converge to form the great cardic vein, middle cardic vein, minor cardic vein and the like and converge to the coronary sinus together with residual venulae to be flown in the right atrium 15. Extremely many veins flow in the coronary sinus and flow-in site is extended over a wide range until nearby the coronary sinus opening 16. Namely, when the balloon is expanded in the inside of the coronary sinus, the blood from venulae converging nearby the coronary sinus opening 16 is not blocked, flows into the right atrium 15 and it is difficult to introduce the blood in the catheter lumen.

Further, since the wall of the coronary sinus is very thin, there is possibility of provoking the damage of wall and perforation by expansion of the balloon. When the damage and perforation are generated, the blood flow out between the heart and pericardial membrane and dangerousness of provoking severe disease such as cardiac tamponade is heightened.

On the other hand, it is very difficult to accurately arrange the balloon at a position surely covering the coronary sinus opening 16 and to arrange the balloon by fixation, because of the influence of cardiac beat. Accordingly, in case of a balloon catheter related to prior art, it is difficult to block the blood flow from the coronary sinus to the right atrium 15 and introduce it to the catheter lumen, and as a result, the capture rate of the contrast medium administrated in the coronary artery is lowered.

Further, when the blood containing the contrast medium administrated in the coronary artery is extracted by the catheter 17 during PCI, it is necessary to introduce devices for blood access such as a sheath introducer and a deployment needle at least at 3 positions, summing a site at which the catheter is inserted, a site where the extracted blood is returned and further, a site to which a guiding catheter used for PCI. Thus, since the number of introducing the devices for blood access is much more than usual PCI, it has been also a problem that the degree of invasion to a patient is high.

DISCLOSURE OF INVENTION

Therefore, considering problems above, the problem to be solved by the present invention is to provide a catheter for extraction that can efficiently extract the blood flowing in the coronary sinus from the coronary artery through the coronary vein and has the same operability as catheters used in conventional PCI. Further, it is also the problem of the invention to provide a catheter for extracorporeal circulation that can lessen the introduction number of the devices for blood access as little as possible and reduce further the burden to a patient, in addition to the same operability as catheters used in conventional PCI.

The present inventors have intensively studied for solving the fore-mentioned problems and as a result, have invented a catheter for extraction being arranged in the biolumen, having distal end and proximal end and for externally extracting the blood from the distal end, wherein the catheter for extraction is equipped with blood extracting lumen in the inside and equipped with a hub at the proximal end portion, and when the minimum sectional area to the circumferential direction of the blood extracting lumen is referred to as S1 and immersion side length is referred to as L1, an equivalent diameter D1 satisfies the formula defined by $D1=(4\times S1)/L1$ and the equivalent diameter D1 is at least 1.80 mm.

The present invention relates to a catheter for extracorporeal circulation having distal end and proximal end, whose distal end is arranged in the coronary sinus of the heart that can return the blood into the body after externally extracting blood from the distal end, wherein the catheter has blood extracting lumen extending from the distal end to the proximal end and blood return lumen extending from the proximal end of the catheter to the fixed length distal end.

When the minimum sectional area to the circumferential direction of the extraction lumen of the catheter for extracorporeal circulation is referred to as S1 and an immersion side length is referred to as L1, an equivalent diameter D1 satisfies the formula defined by $D1=(4\times S1)/L1$ and the equivalent diameter D1 is at least 1.80 mm, and when the minimum sectional area to the circumferential direction of the blood return lumen is referred to as S2 and an immersion side length is referred to as L2, an equivalent diameter D2 satisfies the formula defined by $D2=(4\times S2)/L2$ and the equivalent diameter D2 is at least 1.30 mm and at most 2.00 mm.

In the catheter of the present invention, the circumferential length with which the blood is brought in contact at the minimum sectional area to the circumferential direction of the blood extracting lumen is defined as the immersion side length. Exemplifying one example, when the minimum sectional area to the circumferential direction of the blood extracting lumen is a circle with a diameter of a, a circle ratio is set as $\pi$ and the immersion side length $L1=\pi\times a$, the sectional area $S1=(\frac{1}{4})\times\pi\times a^2$, and the equivalent diameter $D1=a$.

Further, when the minimum sectional area to the circumferential direction of the blood extracting lumen is a square with one side b, the immersion side length $L1=4\times b$, the sectional area $S1=b^2$ and the equivalent diameter $D1=b$.

Further, when the minimum sectional area to the circumferential direction of the blood extracting lumen is a donut shape (provided that $d>c$) that is partitioned by concentric circles with a diameter of c and a diameter of d, the immersion side length $L1=\pi\times(c+d)$, the sectional area $S1=(\frac{1}{4})\times\pi\times(d^2-c^2)$ and the equivalent diameter $D1=d-c$.

Hereat, a side hole is preferably provided at the distal end side of the catheter, the side holes are preferably at least 2 and at most 10, the number of the side hole existing on the same circumference is preferably 1, and the side holes are preferably spirally arranged.

Further, when the sectional area of the side hole is referred to as S3 and the immersion side length is referred to as L3, the equivalent diameter D3 satisfies the formula defined by $D3=(4\times S3)/L3$ and the equivalent diameter D3 is at least 1.80 mm.

Hereat, the catheter is preferably composed of the combination of a braiding tubing complexing metal and a resin and a tube made of a resin, and further, the distal end side is preferably composed of a tube made of a resin. The resin of the tube made of a resin composing the catheter contains preferably an elastomer with a shore hardness of at least 25D and at most 75D, or the blend of the elastomer and the elastomer is further preferably a polyamide elastomer. Further, a substance impermeable for X-ray may be mixed with the resin and hydrophilic coating may be carried out on the external plane of the catheter.

The catheter has preferably a subcatheter detachably installed in the inside of the blood extracting lumen of the catheter, the subcatheter is composed of a flexible tube member and preferably equipped with a hub at the rear end portion, and the tube member is preferably composed of a tube made of a resin. Hereat, the resin of the resin tube composing the subcatheter is preferably either of a high density polyethylene and a low density polyethylene, or either selected from a group comprising a polytetrafluoroethylene (PTFE), a tetrafluoroethylene-perfluoroalkyl vinyl ether copolymer (PFA), a tetrafluoroethylene-hexafluoropropylene copolymer (FEP), a tetrafluoroethylene-ethylene copolymer (ETFE), a polyvinylidene fluoride (PVDF) and a polychlorotrifluoroethylene (PCTFE). A substance impermeable for X-ray may be mixed with the resin and the tube member may be equipped with a marker impermeable for X-ray.

Further, a tip for suppressing the damage of the biolumen is preferably installed on the distal end of the catheter and a tip for suppressing the damage of the biolumen may be installed on the distal end of the subcatheter. Hereat, the tip is composed of a resin, is preferably an elastomer with a shore hardness of at least 25D and at most 40D, or the blend of the elastomers and a substance impermeable for X-ray may be mixed with the resin. Further, the biolumen in which the catheter related to the present invention is deployed is preferably the coronary sinus in particular.

Further, the present invention provides a method of actuating a catheter for extracorporeal circulation, wherein the catheter has distal end and proximal end, the catheter has blood extracting lumen extending from the distal end to the proximal end and blood return lumen extending from the proximal end of the catheter to the fixed length distal end, the blood is extracted from the distal end of the blood extracting lumen arranged in the coronary sinus of patient's heart and the blood is returned from the blood extracting lumen arranged in the body of a patient into the body of the patient.

In this case, when the minimum sectional area to the circumferential direction of the blood extracting lumen of the catheter for extracorporeal circulation is referred to as S1 and the immersion side length is referred to as L1, an equivalent diameter D1 satisfies the formula defined by $D1=(4 \times S1)/L1$ and the equivalent diameter D1 is at least 1.80 mm, and when the minimum sectional area to the circumferential direction of the blood return lumen is referred to as S2 and the immersion side length is referred to as L2, an equivalent diameter D2 satisfies the formula defined by $D2=(4 \times S2)/L2$ and the equivalent diameter D2 is at least 1.30 mm and at most 2.00 mm.

BEST MODE FOR CARRYING OUT THE INVENTION

The various Embodiments of the catheter related to the present invention are illustrated below in details based on the drawings.

Figure 1:
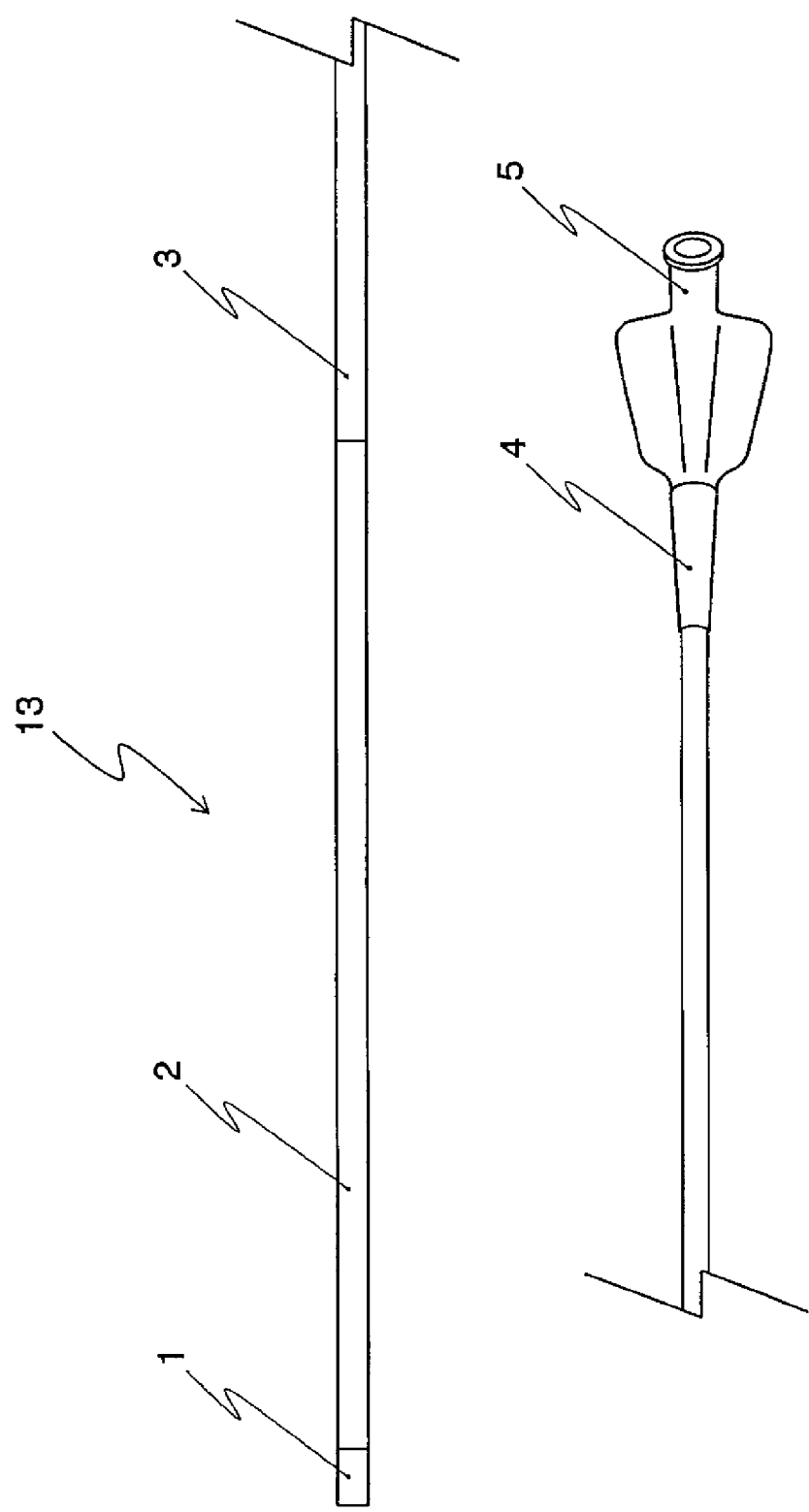
FIG. 1 is a schematic view showing one example of a catheter for extraction of the present invention.

As shown in FIG. 1, the catheter 13 related to the present invention is a catheter for extraction 13 having distal end and proximal end and for externally extracting the blood from the distal end, wherein the catheter 13 for extraction is equipped with blood extracting lumen 6 in the inside and equipped with a hub 5 at the proximal end portion, and when the minimum sectional area to the circumferential direction of the blood extracting lumen 6 is referred to as S1 and an immersion side length is referred to as L1, an equivalent diameter D1 satisfies the formula defined by $D1=(4 \times S1)/L1$ and the equivalent diameter D1 is at least 1.80 mm.

Figure 14:
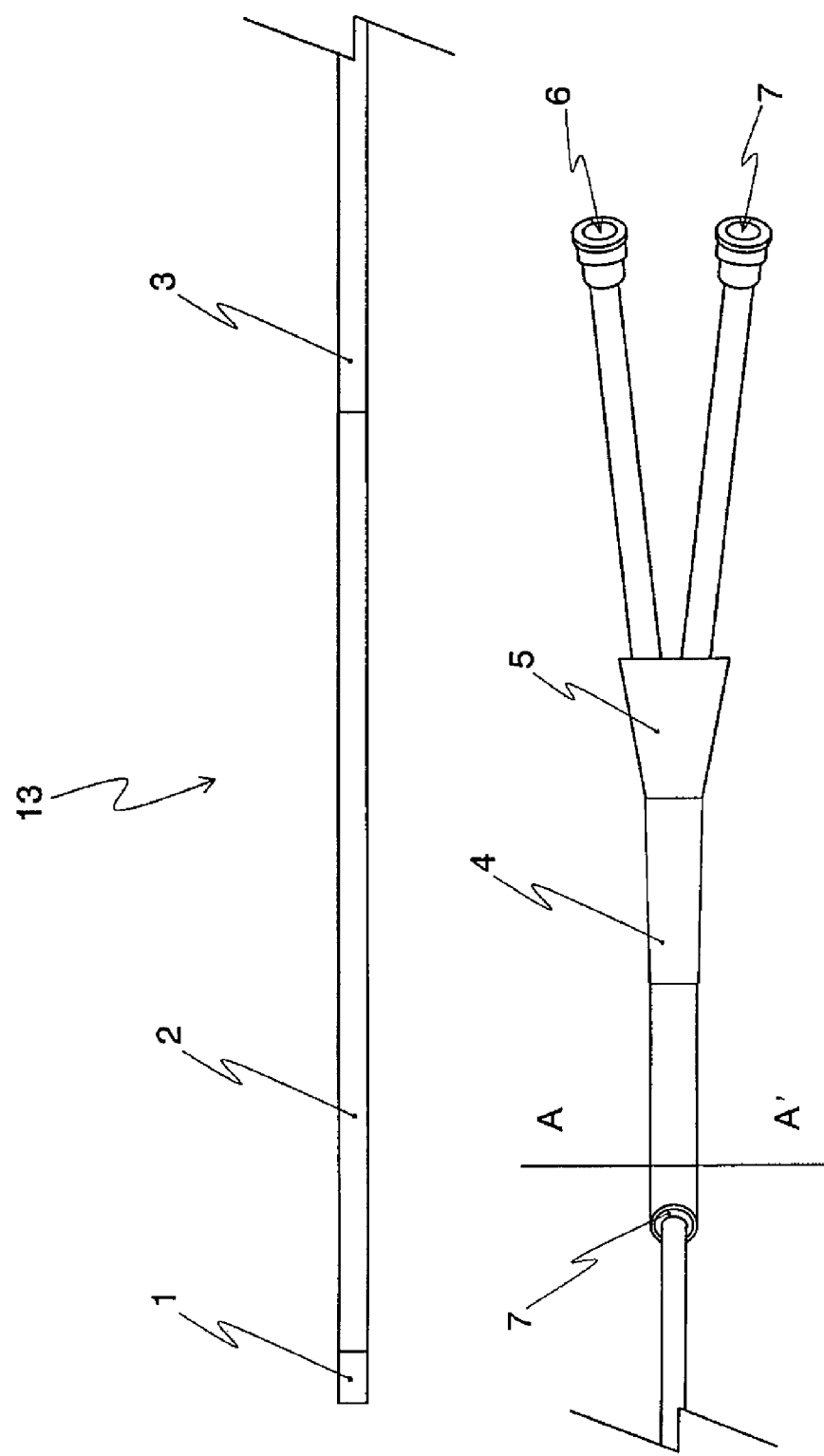
FIG. 14 is a schematic view showing one example of the catheter for extracorporeal circulation of the present invention.

Further, as shown in FIG. 14, other mode of the catheter related to the present invention is a catheter 13 for extracorporeal circulation having distal end and proximal end, whose distal end is arranged in the coronary sinus of the heart that can hydrate the blood into the body after externally extracting blood from the distal end, wherein the catheter 13 has blood extracting lumen 6 extending from the distal end to the proximal end and blood return lumen 7 extending from the proximal end of the catheter 13 to the fixed length distal end.

Since the catheter for extracorporeal circulation related to the present invention is a structure having the blood extracting lumen 6 and the blood return lumen 7 in one catheter, a blood access for returning the blood extracted is not required to be separately provided. Accordingly, the blood access is not required to be separately provided and the degree of invasion to a patient can be more lowered.

On the other hand, since the outer diameter of the catheter is increased by providing the blood extracting lumen and the blood return lumen in one catheter, the number of the blood access is reduced, but there is fear that the degree of invasion to a patient is enhanced by the increase of the outer diameter.

In the catheter 13 for extracorporeal circulation in the present invention, the blood return lumen 7 is extended from the proximal end of the catheter 13 for extracorporeal circulation to the fixed length distal end side and does not reach the distal end of the catheter 13. The increase of the outer diameter of the catheter 13 by adding the blood return lumen 7 can be suppressed by the structure. The full length (a fixed length) of the blood return lumen 7 is preferably as short as possible within a range at which the distal end of the blood return lumen 7 can be inserted in the body. The full length (a fixed length) of the blood return lumen 7 is different depending on a shape of the hub 5 and the effective length (the length of a portion inserted in the body) of the catheter 13 for extracorporeal circulation, but at least 100 mm and at most 700 mm is preferable.

The catheter 13 for extracorporeal circulation in the present invention is characterized in that when the minimum sectional area to the circumferential direction of the blood extracting lumen 6 of the catheter for extracorporeal circulation is referred to as S1 and an immersion side length is referred to as L1, an equivalent diameter D1 satisfies the formula defined by D1=(4×S1)/L1 and the equivalent diameter D1 is at least 1.80 mm, and when the minimum sectional area to the circumferential direction of the blood return lumen 7 is referred to as S2 and the immersion side length is referred to as L2, an equivalent diameter D2 satisfies the formula defined by D2=(4×S2)/L2 and the equivalent diameter D2 is at least 1.30 mm and at most 2.00 mm.

The minimum sectional area to the circumferential direction mentioned here indicates a sectional area that is minimum to the length direction of the catheter, among the sectional area to the circumferential direction of the blood extracting lumen 6 extending in the catheter or that of the blood return lumen 7.

The sectional area to the circumferential direction is measured by cutting the catheter to the circumferential direction and observing the blood extracting lumen 6 or the blood return lumen 7 at the cutting plane in magnification with a micro high scope and the like. The minimum value obtained by carrying out similar measurements at a plural number of spots to the length direction of the catheter is the minimum sectional area to the circumferential direction. The more plentiful the measurement spots to the length direction are, the higher the precision of the minimum sectional area to the circumferential direction is. The evaluation value of the minimum sectional area to the circumferential direction mentioned in this specification is a value determined by evaluation by every length of 10 mm.

The immersion side length mentioned here indicates the sum of the length of periphery partitioning respective lumens 6 and 7 in the section to the circumferential direction of the blood extracting lumen 6 or that of the blood return lumen 7 extending in the catheter 13. For example, when the blood extracting lumen 6 is a circle with a diameter of R (see FIG. 16), the immersion side length L1 is π×R. Further, when the blood extracting lumen 6 is a donut shape that is partitioned by a circle with a diameter of R and a circle with a diameter of r (R>r) concentrically arranged, the immersion side length is π×(R+r).

The immersion side length is measured by cutting the catheter 13 to the circumferential direction and observing the blood extracting lumen 6 or the blood return lumen 7 at the cutting plane in magnification with a micro high scope and the like.

The behavior of the extraction and return of the blood through a catheter can be hydrodynamically estimated. When fluid such as the blood flows in a tube such as a catheter 13, Reynolds number Re being dimensionless quantity representing flow in a tube is represented as the formula 1. Wherein the minimum sectional area to the circumferential direction of the blood extracting lumen 6 is referred to as S1, the flow rate of the blood in the blood extracting lumen 6 as U1, the immersion side length as L1, the equivalent diameter as D1, the density of the blood as ρ and the viscosity of the blood as μ.

$$Re=(D1 \times U1 \times \rho)/\mu=[(4 \times S1)/L1] \times (\rho/\mu) \quad \text{(Formula 1)}$$

Similarly, when the minimum sectional area to the circumferential direction of the blood return lumen 7 is referred to as S2, the flow rate of the blood in the blood return lumen 7 as U2, the immersion side length as L2 and the equivalent diameter as D2, the Reynolds number Re is represented as the formula 2.

$$Re=(D2 \times U2 \times \rho)/\mu=[(4 \times S2)/L2] \times (\rho/\mu) \quad \text{(Formula 2)}$$

It has been known that a case of the Reynolds number of less than 2,100 is laminar flow and a case of that exceeding 4,000 is turbulent flow. When the minimum sectional shape to the circumferential direction of the blood extracting lumen 6 or the blood return lumen 7 is assumed as a circle with a diameter of 3 mm, the Reynolds number is about several ten orders. Accordingly, it is considered that the flow of the blood in the blood extracting lumen 6 and the blood return lumen 7 is laminar flow.

With respect to the laminar flow in the tube, the formula of Hagen-Poiseuille shown in the formula 3 consists. Wherein the equivalent diameter of the blood extracting lumen 6 is referred to as D1, the length of the blood extracting lumen 6 as Lu1, the absolute value of pressure difference (hereinafter, referred to as extracting pressure) provided at extraction as ΔP1 and extracting amount as Q1. The extracting pressure in the present invention is pressure difference P1−P0 when pressure when the extracting amount is 0 mL/min is referred to as P0 mmHg and pressure when the extracting amount is Q1 mL/min (Q1>0) is referred to as P1 mmHg.

$$Q1=[\pi \times (D1/2)^4 \times \Delta P1]/(8 \times \mu \times Lu1) \quad \text{(Formula 3)}$$

Similarly, when the equivalent diameter of the blood return lumen 7 is referred to as D2, the length of the blood return lumen 7 as Lu2, the absolute value of pressure difference (hereinafter, referred to as returning pressure) provided at hydration as ΔP2 and returning amount as Q2, the formula 4 consists. The returning pressure in the present invention is pressure difference P2−P0 when pressure when the returning amount is 0 mL/min is referred to as P0 mmHg and pressure when the returning amount is Q2 mL/min (Q2>0) is referred to as P2 mmHg. With respect to the extracting amount and returning amount, the formula 5 consists from the continuous formula.

$$Q2=[\pi \times (D2/2)^4 \times \Delta P2]/(8 \times \mu \times Lu2) \quad \text{(Formula 4)}$$

$$Q1=Q2 \quad \text{(Formula 5)}$$

When the blood containing a contrast medium administrated to the coronary artery is extracted from the coronary sinus and the blood removing the contrast medium by an extracorporeal circulation therapy such as adsorption is hydrated into the body, it is preferable for efficiently carrying out the removal of the contrast medium that extracting amount is higher. Although the lower the extracting amount is, the higher the adsorption efficiency is, it becomes difficult to extract all of the blood flown into the coronary sinus from the coronary artery when the extracting amount is too low and as a result, the efficiency of removal of the contrast medium is lowered. Accordingly, the extracting amount is preferably at least 25 mL/min and more preferably at least 50 mL/min. At least 80 mL/min is further preferable. As a method of raising the extracting amount, there is a method of increasing extracting pressure using means such as a pump and a syringe or a method of enlarging the equivalent diameter of the blood extracting lumen 6. The extracting pressure is more negative pressure in accordance with the increase of extracting pressure. When the extracting pressure is lower than −200 mg, the possibility of collapse of the blood vessel is extremely high because of negative pressure and it is dangerous; therefore at least −200 mmHg is preferable. The extracting pressure is preferably at least −150 mmHg from the viewpoint of preventing the flattening of the blood vessel and more preferably at least −100 mmHg.

In order to keep the extracting amount at 80 mL/min or more under the condition of an extracting pressure of at least −100 mmHg, the equivalent diameter D1 of the blood extracting lumen 6 is preferably at least 1.80 mm. When D1 is less than 1.80 mm, it is difficult to stably obtain the extracting amount of at least 80 mL/min under the condition of an extracting pressure of at least −100 mmHg. It is preferable from the viewpoint of the extracting amount that D1 is larger, but the larger the D1 is, the larger the size of a device for blood access such as a sheath introducer for inserting the catheter 13 is; therefore the degree of invasion to a patient is heightened. D1 may be at most 3.00 mm from this viewpoint.

Further, it is preferable from the formula 5 that the returning amount is at least 25 mL/min and at least 50 mL/min is more preferable. At least 80 mL/min is more preferable. In accordance with the increase of the returning amount, the returning pressure is positive pressure. Since dangerousness of generating hemolysis by the raising of the returning pressure is enhanced, at most 300 mmHg is preferable. At most 200 mmHg is more preferable and at most 100 mmHg is further preferable.

The equivalent diameter D2 of the blood return lumen 7 is preferably at least 1.30 mm and at most 2.00 mm so that the returning pressure is less than at most 100 mmHg and the returning amount is at least 80 mL/min. When D2 is less than 1.30 mm, it is difficult to keep the returning amount at 80 mL/min or more. On the other hand, when D2 exceeds 2.00 mm, the outer diameter of the catheter 13 is remarkably increased, it is not preferable because the degree of invasion to a patient is heightened.

Figure 15:
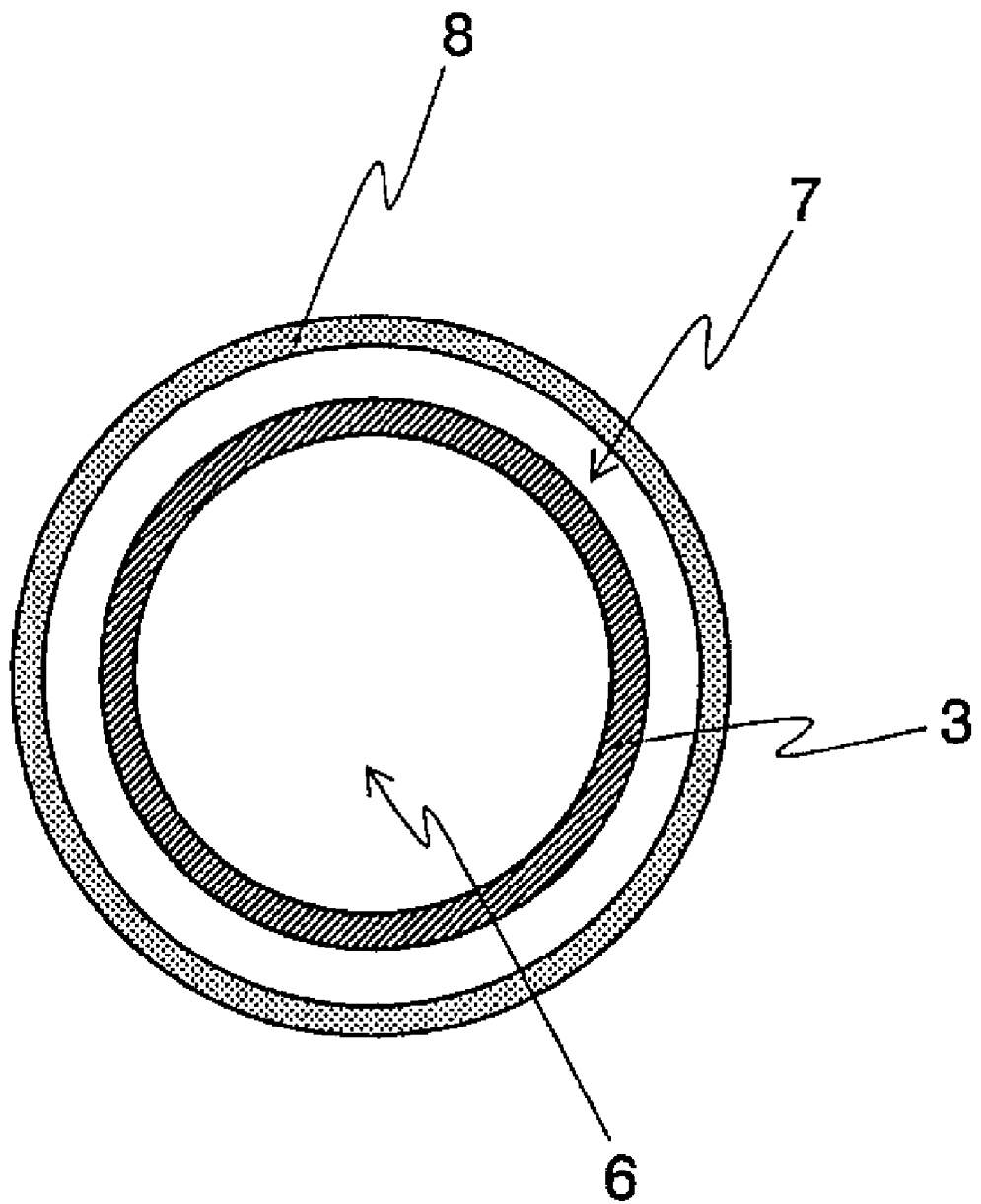
FIG. 15 is a sectional view showing one example of the A-A' section of the catheter in FIG. 14 for extracorporeal circulation of the present invention.
Figure 16:
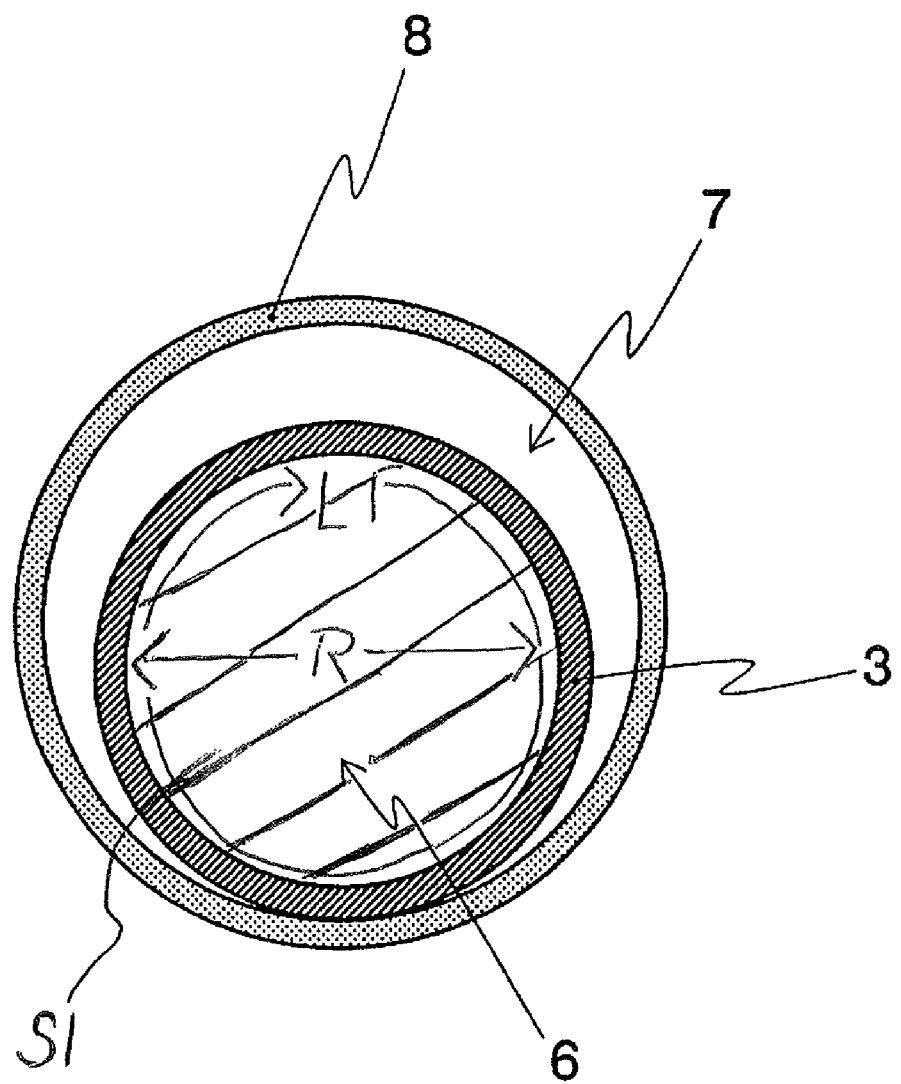
FIG. 16 is a sectional view showing one different example of the A-A' section of the catheter for extracorporeal circulation of the present invention.
Figure 17:
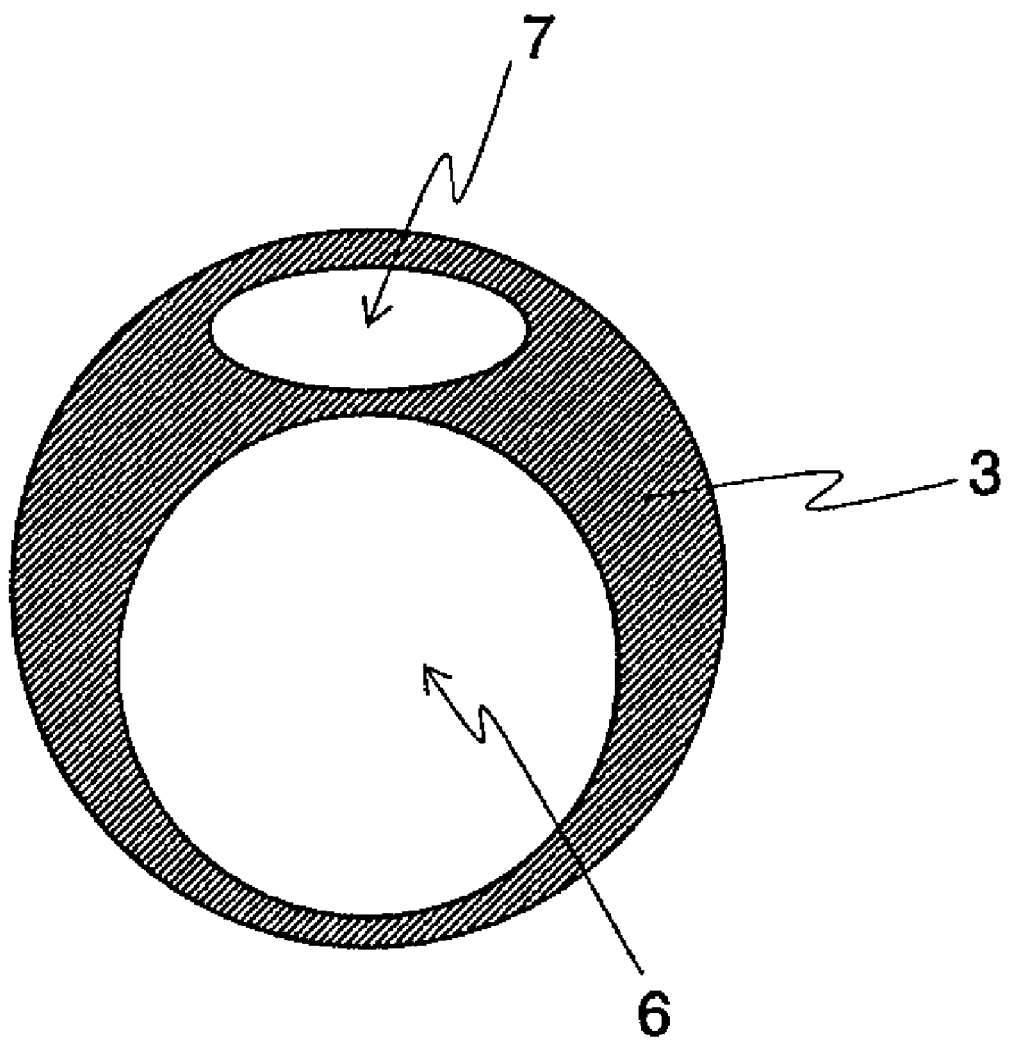
FIG. 17 is a sectional view showing one different example of the A-A' section of the catheter for extracorporeal circulation of the present invention.
Figure 18:
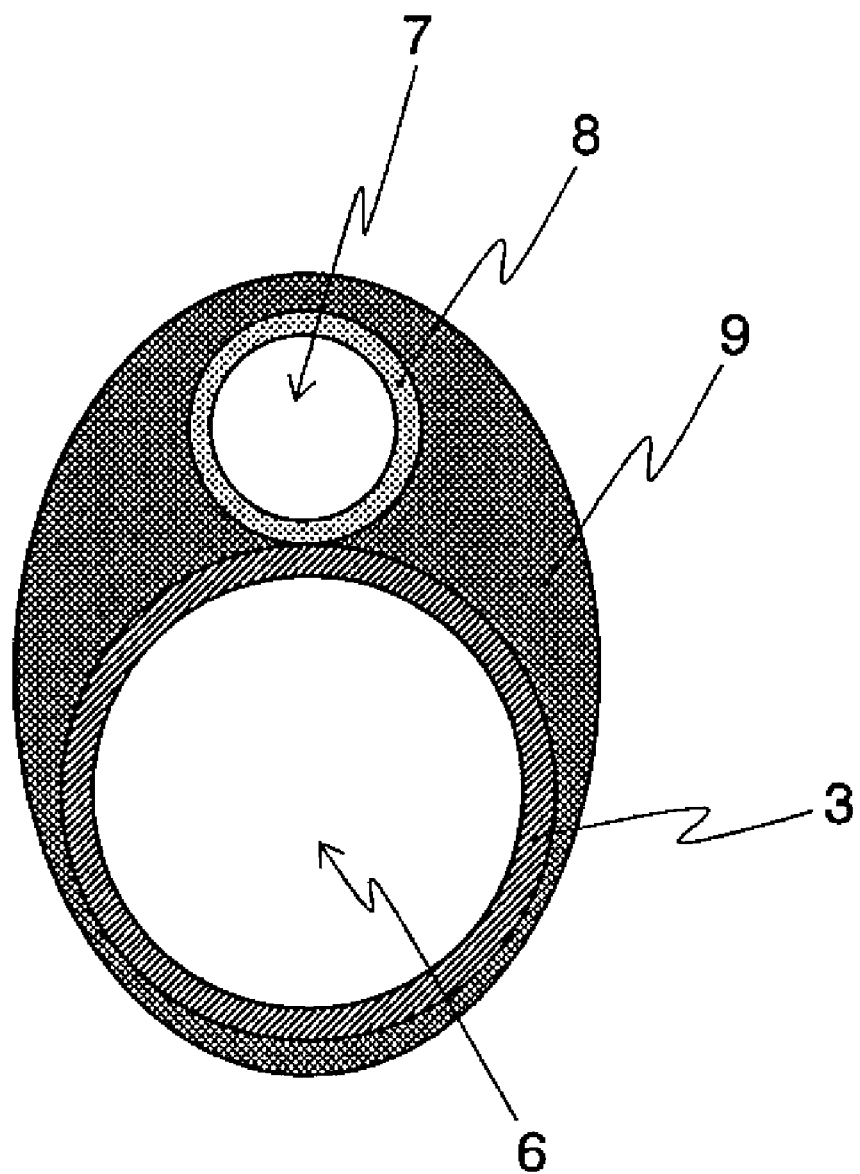
FIG. 18 is a sectional view showing one different example of the A-A' section of the catheter for extracorporeal circulation of the present invention.

As described above, the other mode of the catheter related to the present invention is characterized in that it has both of the blood extracting lumen 6 and the blood return lumen 7 in one catheter as shown in FIG. 14. The structure for providing the lumens 6 and 7 is not limited. Namely, the structure includes a structure in which an outside tube 8 is arranged in a double tube shape at the outside of the braiding tube 3 as shown in FIGS. 15 and 16, a structure in which the braiding tube 3 is biaxial as shown in FIG. 17, a structure in which the outside tube 8 is arranged at the outside of the braiding tube 3 in parallel and they are fixed with a covering tube 9 as shown in FIG. 18, etc. In particular, in case of the structure as shown in FIGS. 15 and 16, it is preferable that a lumen partitioned with the outside plane of the braiding tube 3 and the inside plane of the outside tube 8 is set as the blood extracting lumen 6 and a lumen partitioned at the inside plane of the braiding tube 3 is set as the blood return lumen 7 in order to secure stably the extracting amount.

Figure 4:
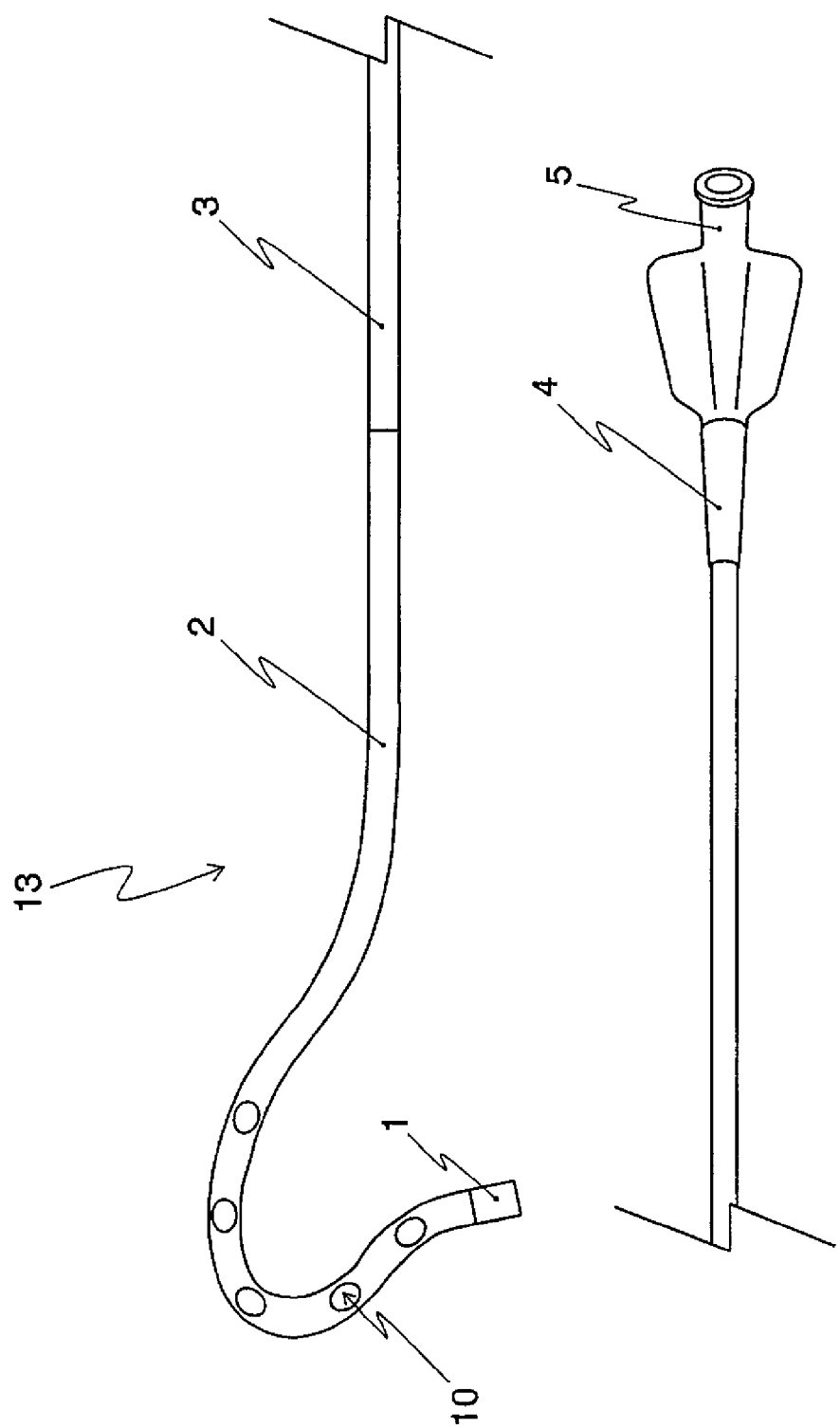
FIG. 4 is a schematic view showing one example having side holes among a catheter for extraction of the present invention.
Figure 21:
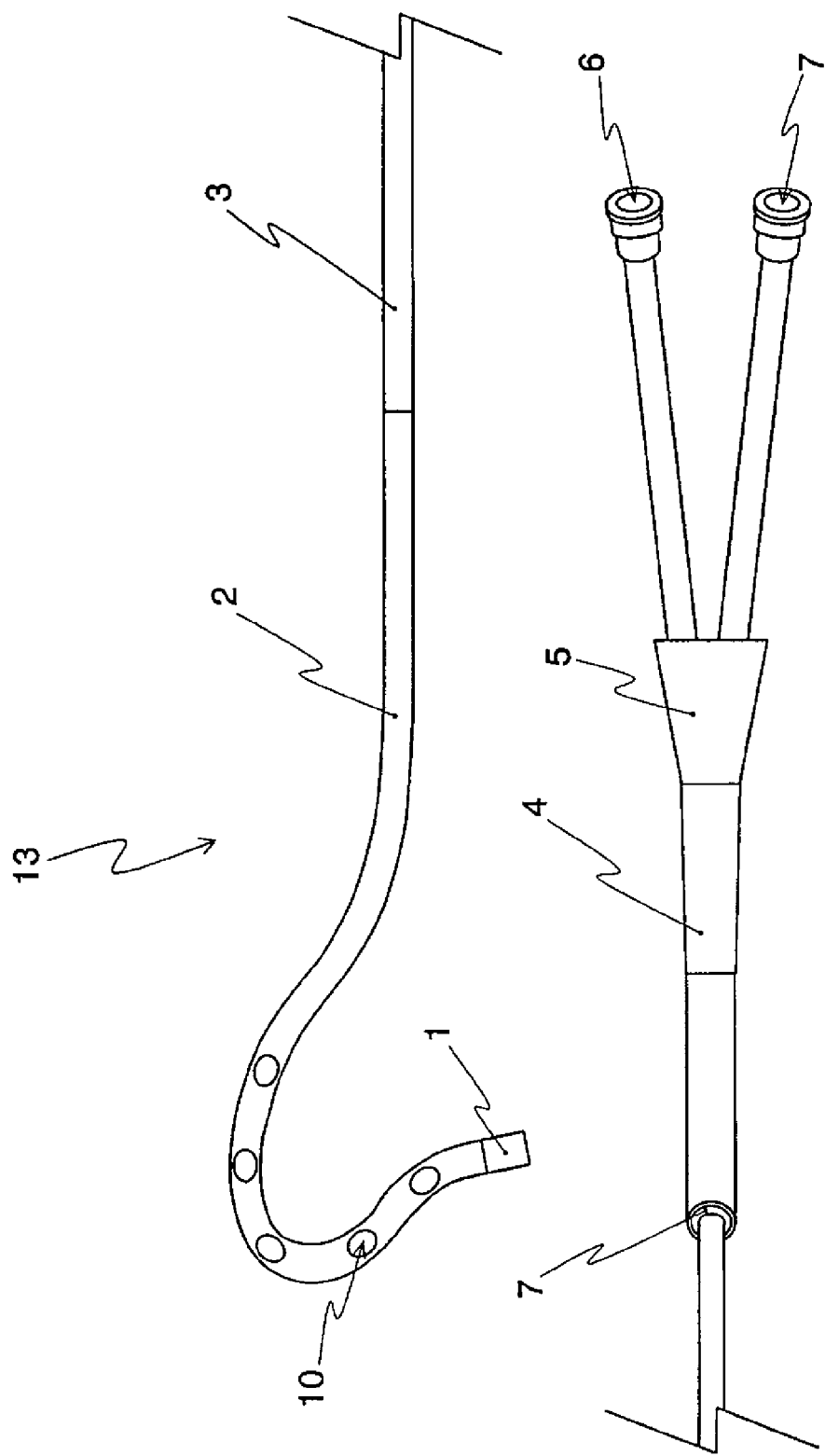
FIG. 21 is a schematic view showing one example having side holes among the catheter for extracorporeal circulation of the present invention.

As shown in FIGS. 4 and 21, it is preferable that the distal end side of the catheter 13 for extracorporeal circulation and preferably a site inserted into the coronary sinus are equipped with side holes 10. When the catheter 13 for extracorporeal circulation is inserted in a site enclosed by very thin wall such as the coronary sinus and arranged to carry out extraction, the distal end portion of the catheter 13 adheres occasionally with peripheral wall because of the influence of the extracting pressure. Because of the adherence, the necessary extracting amount is not only realized but also dangerousness of provoking the damage and perforation of surrounding wall is enhanced and it is dangerous. Although the possibility of adherence with peripheral wall is lowered by setting the equivalent diameter of the distal end portion of the catheter 13 as at least 1.80 mm, the possibility is preferably reduced more by providing the side holes 10.

The side holes 10 are preferably at least 2 in order to more effectively prevent the adherence with peripheral wall. The safety of the extraction of the blood is further enhanced by providing a plural number of the side holes 10.

On the other hand, since the strength of a portion at which the side holes 10 are provided is lowered by the increase of the number of the side holes 10, the side holes 10 are preferably at most 10. Further, although the flexibility of the catheter 13 at the portion is improved by providing the side holes 10, kink resistance is lowered. Consequently, the number of the side holes 10 existing on the same circumference is preferably one in order to make the most use of merit by providing the side holes 10 without providing kink to the catheter 13. Since the dangerousness of kink and further plasmotomy of the catheter 13 is increased by increasing the number of the side holes 10 existing on the same circumference, it is not preferable.

Figure 5:
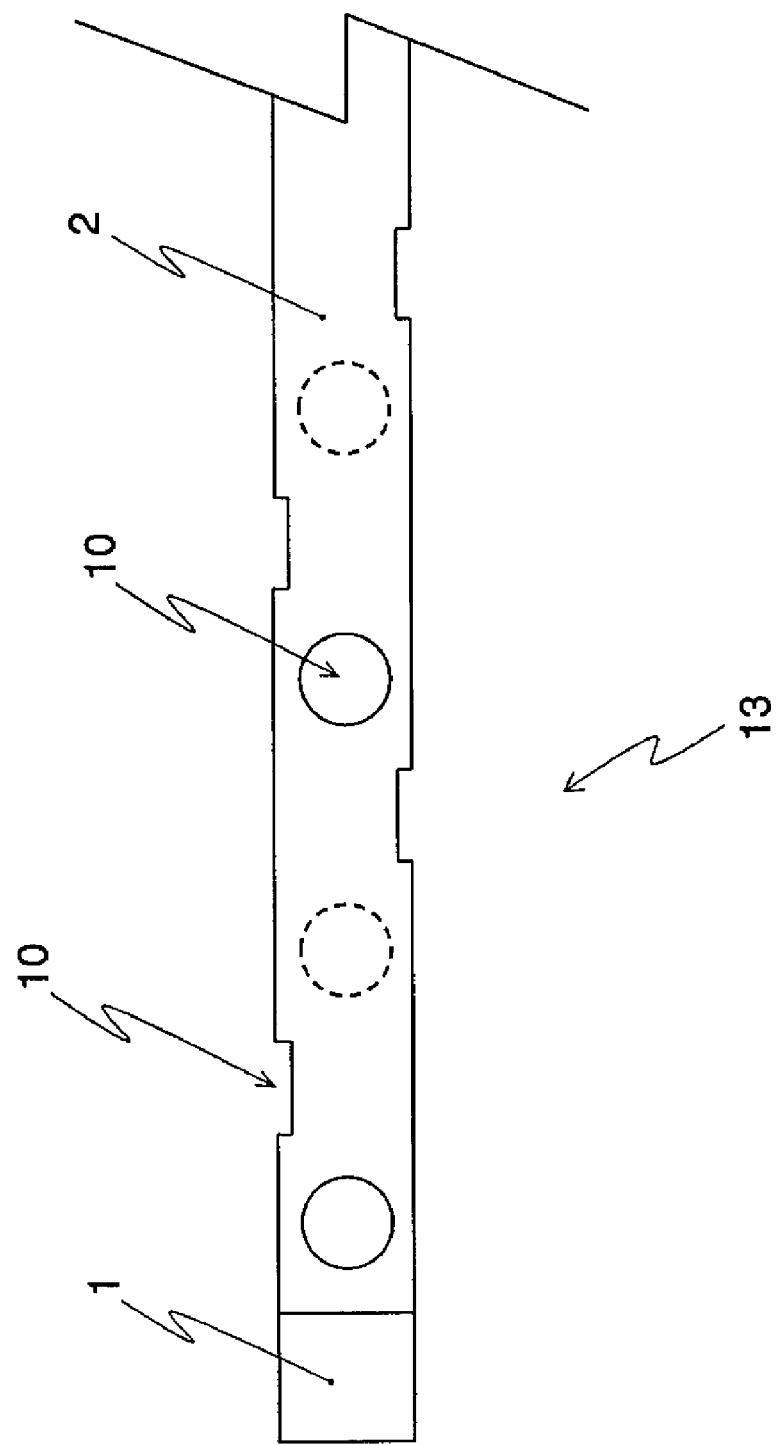
FIG. 5 is a schematic view showing one example of the distal end side of the catheter of the present invention.

The pattern by which the side holes 10 are arranged does not limit the effect of the present invention so far as at least 2 of them do not exist on the same circumference. Namely, a pattern of linearly arranging a plural number of the side holes 10 to an axial direction, a pattern of being spirally arranged as FIG. 5, and the like are preferable. They are preferably arranged spirally from the viewpoint of preventing adherence with the wall around the coronary sinus. Hereat, the number of the side holes 10 per unit spiral and the slant of spiral can be designed matching with the dimension and the shape of the distal end portion of the catheter 13 for extracorporeal circulation.

Further, the equivalent diameter D3 of the side holes 10 is preferably at least 1.80 mm. When D3 is less than 1.80 mm, it is difficult to secure the extracting amount of at least 80 mL/min under the condition of an extracting pressure of at least −100 mmHg. It is preferable from the viewpoint of the extracting amount that D3 is larger, but when D3 is larger than D1, the strength of a portion at which the side holes 10 exist is extremely lowered. D3 may be at most 3.00 mm from this viewpoint.

Figure 6:
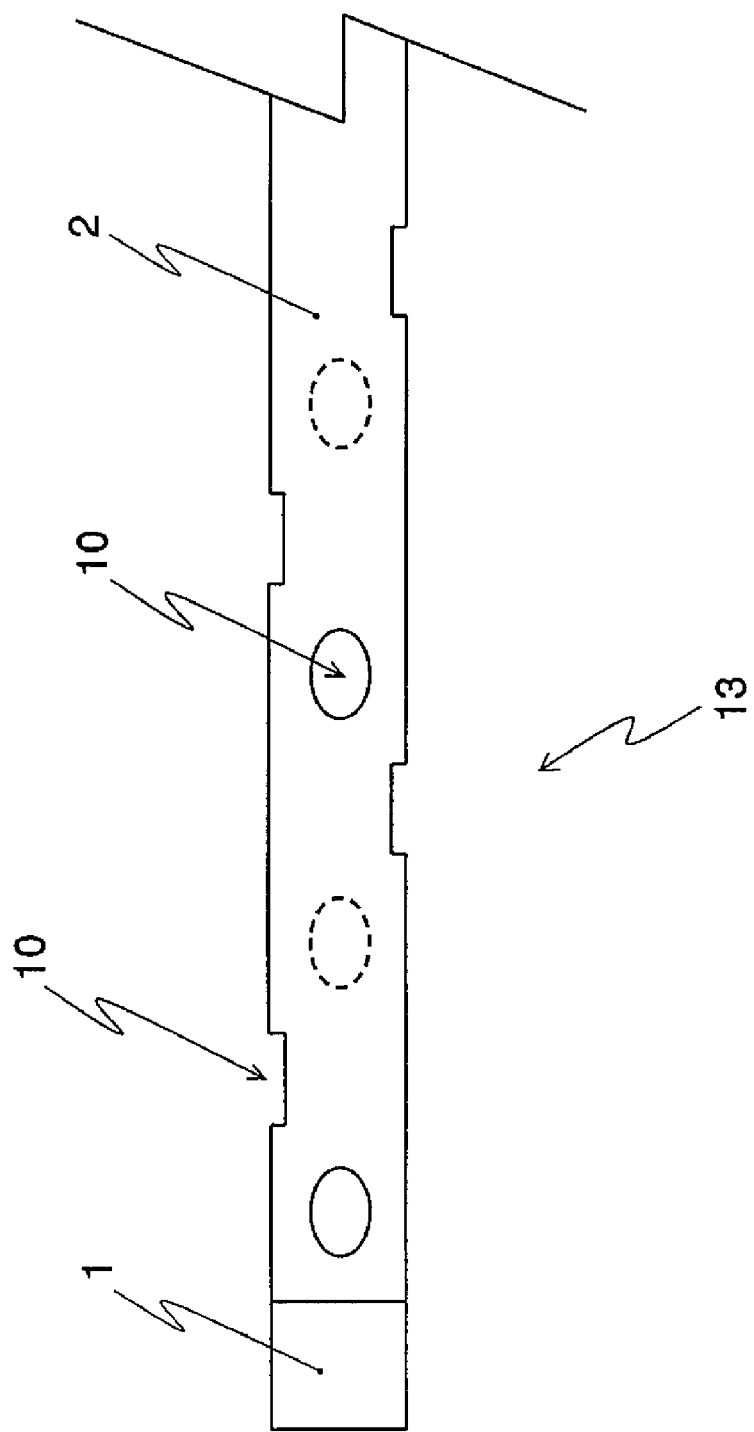
FIG. 6 is a schematic view showing one different example of the distal end side of the catheter of the present invention.

The shape of the side holes 10 does not prevent the effect of the present invention and an arbitrary shape can be selected considering the flexibility, strength and the like of the catheter 13. Namely, it may be shapes such a circular shape (FIG. 5), an elliptical shape (FIG. 6), and a rectangular shape. In case of an elliptical shape, a long axis direction may be the axial direction of the catheter and may be a circumferential direction. Further, in case of a rectangular shape, a long side direction may be the axial direction of the catheter and may be a circumferential direction. Further, it is not necessary that the shapes of all of the side holes 10 are the same shape and a combination of shapes such as a circular shape, an elliptical shape and a rectangular shape may be used. The shape of the side holes 10 is preferably a circular shape or an elliptical shape considering the easiness of processing, the transformation of shape of the side holes 10 when the catheter 13 is bent, etc.

The method of providing the side holes 10 does not limit the effect of the present invention. Laser processing such as YAG laser, excimer laser and femtosecond laser, cutting processing such as punching and the like are preferably used. Surface treatment such as thermal treatment and polishing treatment may be carried out after processing.

The catheter 13 related to the present invention is used in combination at PCI and percutaneously introduced into the coronary sinus from the femoral region, the cervical region, the arm region and the like; therefore an effective length of at least 500 mm is preferable and an effective length of at least 800 mm is more preferable. It is necessary to provide torque and carry out operations such as rotation and pushing in order to introduce the catheter 13 having comparatively long effective length into the coronary sinus. Accordingly, the transmission property of torque is requested for the catheter 13 related to the present invention. Further, flexibility is also required in order to introduce it into the coronary sinus through flexible and bent blood vessel.

Even if the catheter 13 is arranged at the bent portion of the coronary sinus, the catheter 13 does not kink and the adequate blood extracting lumen 6 must be secured in order to realize stable extracting amount. Further, the securement of the blood return lumen 7 is also important for realizing stable returning amount. Therefore an adequate kink resistance is required for the catheter 13. From above reasons, the catheter 13 for extracorporeal circulation related to the present invention is preferably composed of the combination of the braiding tubing 3 complexing metal and a resin the tube 2 made of a resin. The transmission of torque, kink resistance and flexibility are simultaneously secured by using the braiding tube 3. The method of combination is not specifically limited, but a tube 2 made of a resin at the distal end side and the braiding tube 3 at the proximal end portion are preferably arranged from the viewpoint that the distal end side is flexible and the proximal end side is rigid.

The introduction of the catheter 13 into the coronary sinus is carried out through the vein. Since the wall of vein is thin in comparison with the wall of the artery, the distal end side of the catheter 13 is preferably composed of the tube 2 made of a resin. Flexibility is greatly improved by using the tube 2 made of a resin at the distal end portion in comparison with a case of preparing the whole of the catheter 13 with the braiding tube 3, and the catheter 13 can be safely introduced into the coronary sinus. The length of the tube 2 made of a resin provided at the distal end side is selected depending on the shape of the coronary sinus, but at least 50 mm and at most 200 mm is preferable. When it is shorter than 50 mm, adequate flexibility is not exhibited; therefore dangerousness of damaging the coronary sinus is high and it is not preferable. Further, when it is longer than 200 mm, it is not preferable that the transmission of torque to the distal end side of the catheter 13 is inadequate and insertion to the coronary sinus is difficult.

Figure 2:
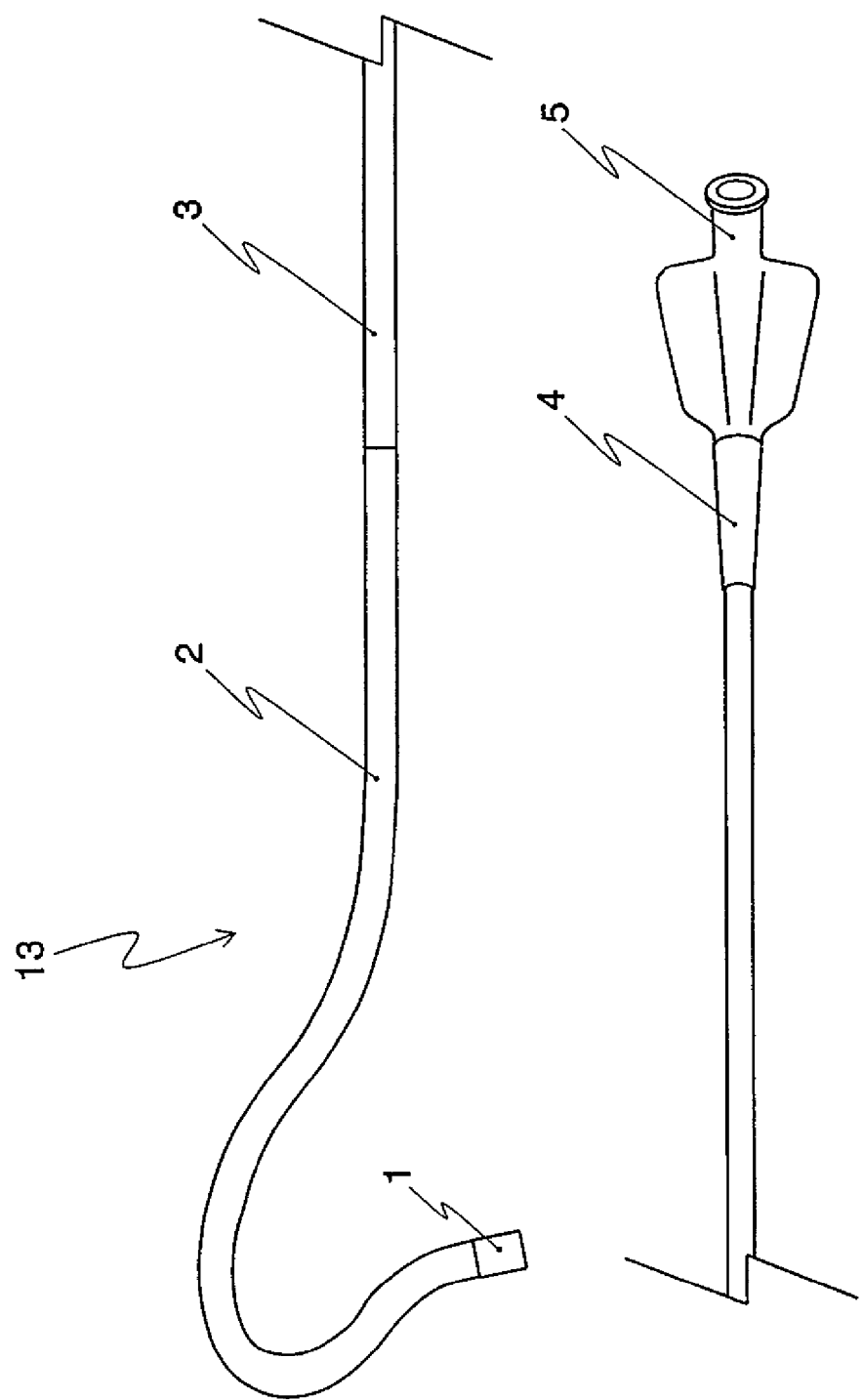
FIG. 2 is a schematic view showing one different example of a catheter for extraction of the present invention.
Figure 3:
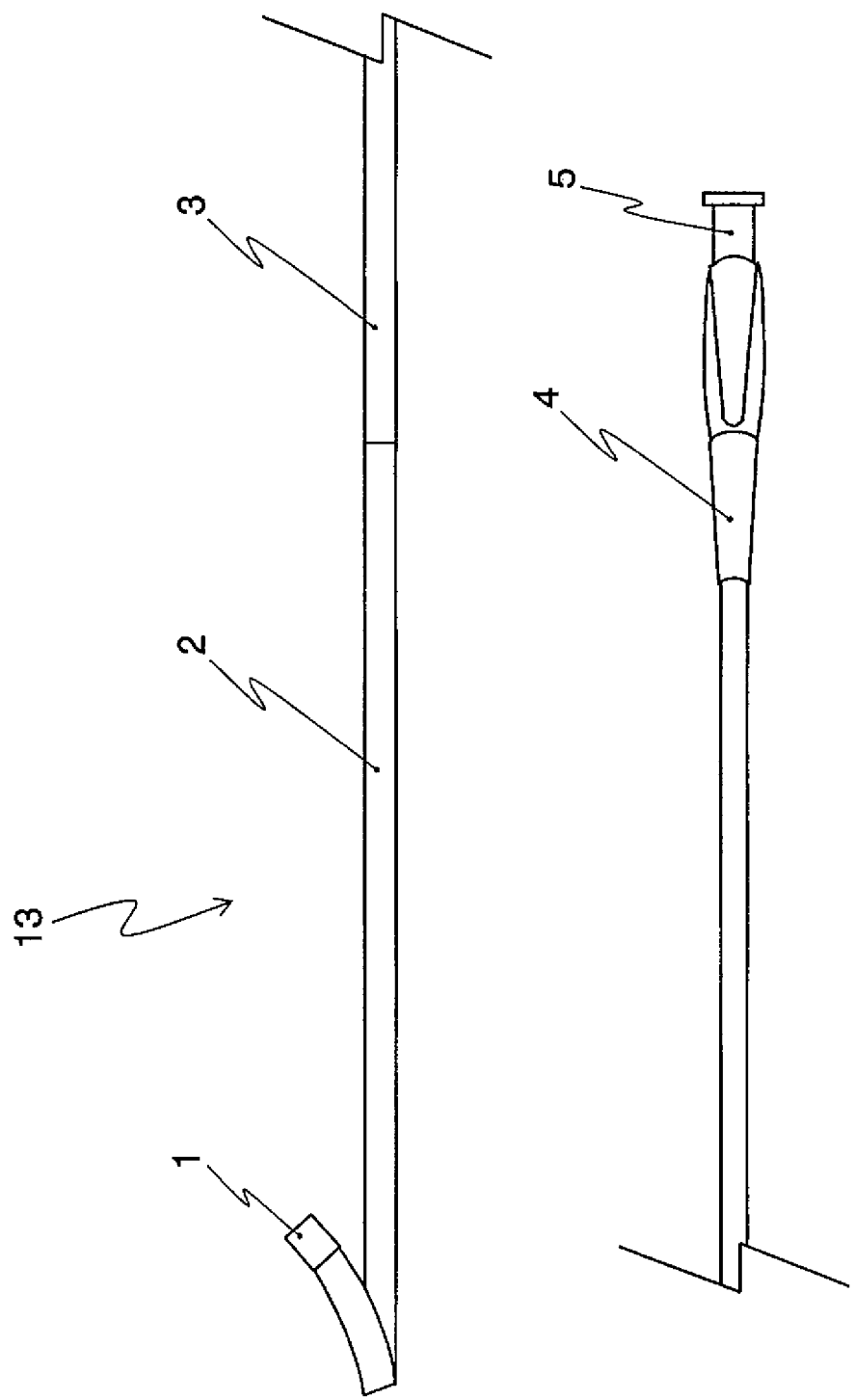
FIG. 3 is a side view showing one example of a catheter for extraction shown in FIG. 2.
Figure 19:
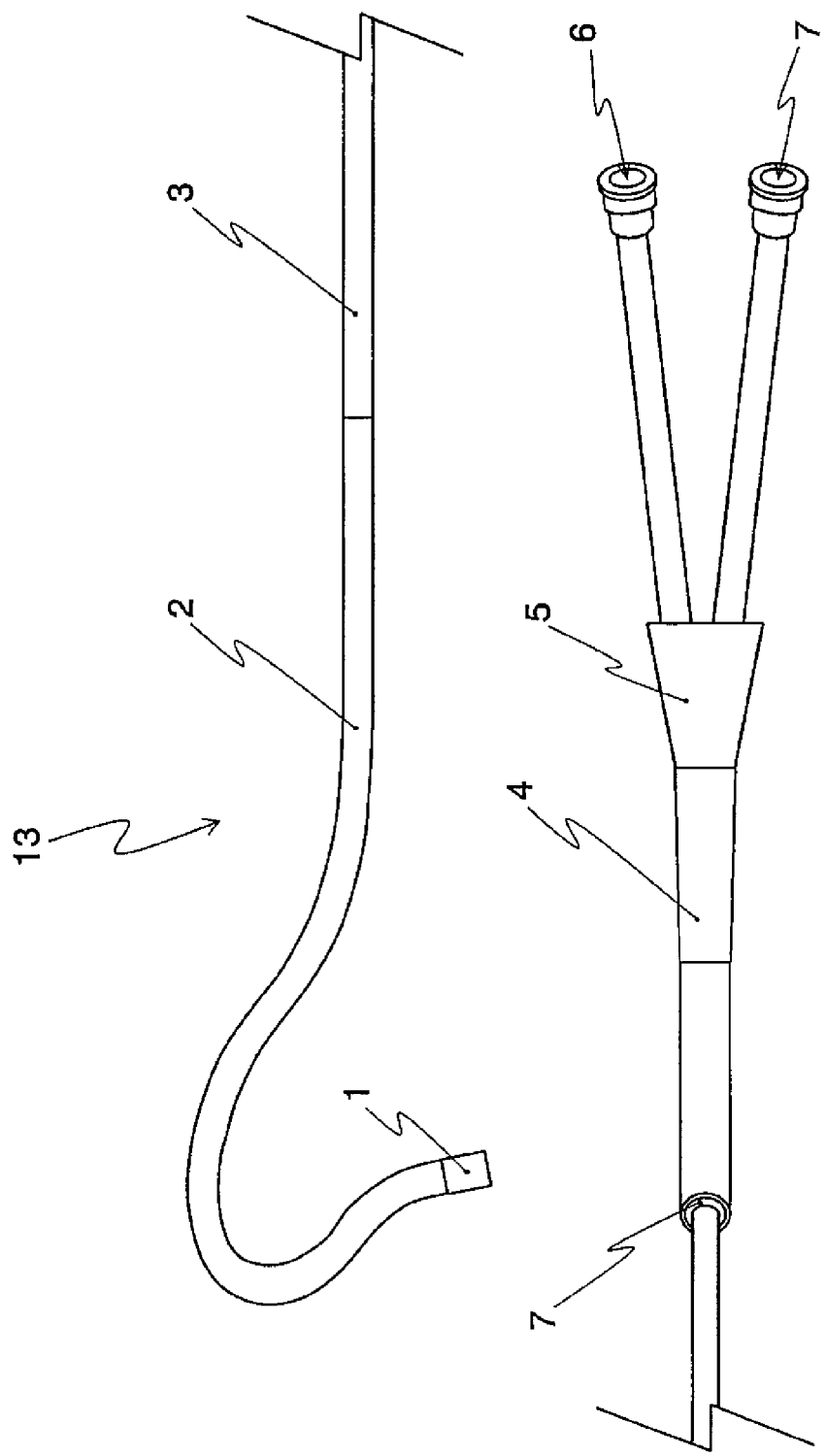
FIG. 19 is a schematic view showing one different example of the catheter for extracorporeal circulation of the present invention.
Figure 20:
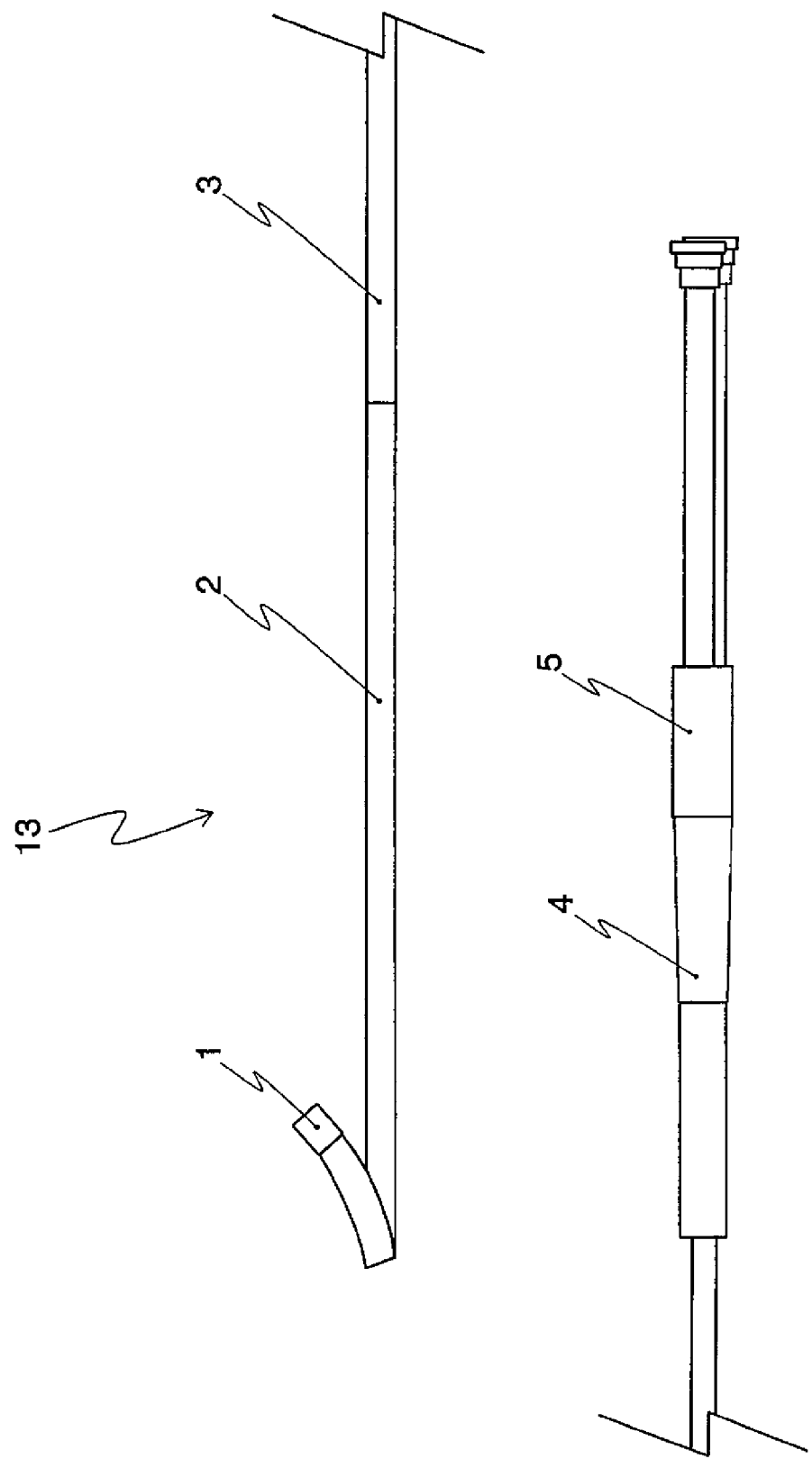
FIG. 20 is a side view showing one example of the catheter for extracorporeal circulation shown in FIG. 19.

Further, as shown in FIGS. 2 and 19, the distal end side of the catheter 13 may be preliminarily processed to an arbitrary shape in order to make the easy introduction to the coronary sinus. FIGS. 2 and 19 show examples provided with three greatly bent shapes, but the number and shape of the bending are not limited. Further, the examples of FIGS. 2 and 19 provide a bent shape on the same plane, but the bent shape may be shown on not only the same plane but also over a plural number of planes, as shown in FIGS. 3 and 20.

The method of providing the bent shape does not limit the effect of the present invention and all process methods can be utilized. As a preferable example, there is mentioned a method of providing an objective bent shape after insertion of a core material for keeping the shape of the lumen 6 for extraction and memorizing the shape by thermal treatment.

The resin composing the braiding tube 3 or the resin composing the tube 2 made of a resin contains preferably an elastomer with a Shore hardness of at least 25D and at most 75D or the blend of the elastomers. The Shore hardness mentioned in the present invention is a value measured according to ISO868. The compatibility of strength and flexibility is easy by using the elastomer. In particular, the flexibility can be easily realized by using the elastomer or the blend of the elastomers on an external plane in case of the braiding tube 3.

When only an elastomer with a Shore hardness of less than 25D is used, it is not preferable because strength is difficult to be kept. When only an elastomer with more than 75D is used, it is not preferable because the flexibility is lowered. The elastomer may be blended at an arbitrary ratio for realizing objective strength and flexibility. The resins used for the braiding tube 3 and the tube 2 made of a resin may be the same elastomer and may be different elastomer, but the different elastomer is preferably used for easily controlling the physical properties of the catheter 13 for extracorporeal circulation. It is unnecessary to use the same resin over the full length of the braiding tube 3 or the tube 2 made of a resin and gradient may be provided for physical properties to the length direction of the tubes 2 and 3 using a plurality of resins. As a preferable example, the resin used for the braiding tube 3 is a resin with a Shore hardness of at least 40D and at most 75D and the resin used for the tube 2 made of a resin is a resin with a Shore hardness of at least 25D and at most 63D.

Hereat, considering processability and the like, the elastomer is preferably a polyamide elastomer.

The preparation process of the braiding tube 3 and the tube 2 made of a resin does not limit the effect of the present invention. The braiding tube 3 is prepared by braiding a metal wire on the external face of a tube by fluorine resins such as a polytetrafluoroethylene (PTFE), a tetrafluoroethylene-perfluoroalkyl vinyl ether copolymer (PFA), a tetrafluoroethylene-hexafluoropropylene copolymer (FEP), a tetrafluoroethylene-ethylene copolymer (ETFE), a polyvinylidene fluoride (PVDF) and a polychlorotrifluoroethylene (PCTFE) and polyamide elastomers and the like, or carrying out coil processing and coating the elastomer or the blend of the elastomers on its external surface. As the metal wire or the material of a coil, stainless alloy, cobalt-chromium alloy, nickel-titanium alloy and the like can be used, and its sectional shape may be arbitrary shapes such as a circular shape, an elliptical shape and a rectangular shape. The tube 2 made of a resin can be prepared by an extrusion molding process, a dipping process, an electric wire coating process and the like.

Figure 7:
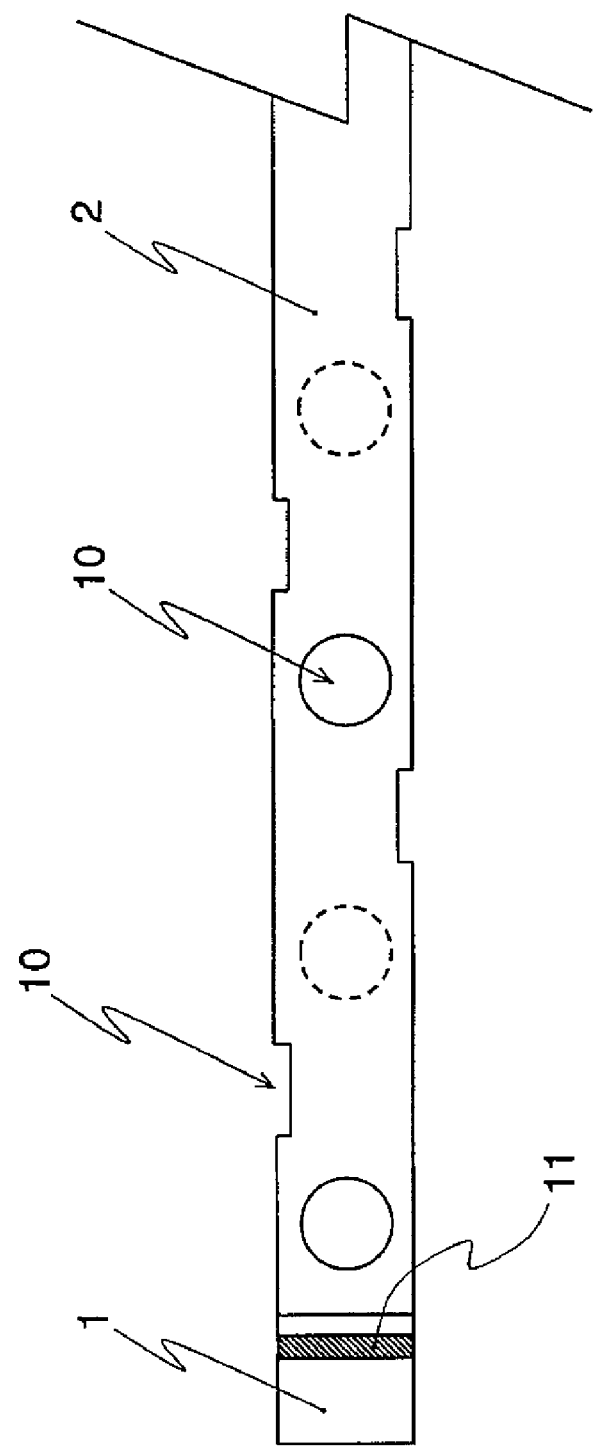
FIG. 7 is a schematic view showing one different example of the distal end side of the catheter of the present invention.
Figure 8:
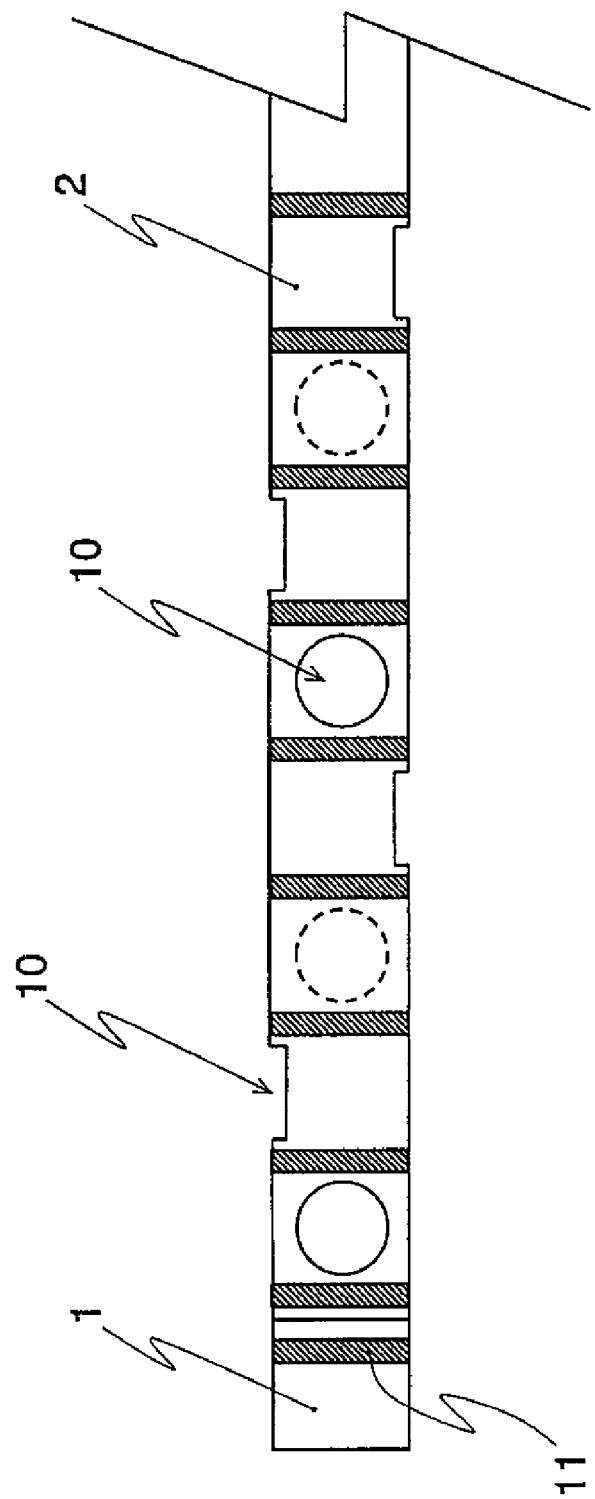
FIG. 8 is a schematic view showing one different example of the distal end side of the catheter of the present invention.

The catheter 13 is introduced into the coronary sinus under X-ray fluoroscopic control. Accordingly, the catheter 13 has preferably X-ray impermeability. The method of providing the X-ray impermeability includes a method of providing a marker 11 composed of a material having the X-ray impermeability on the external surface or inner surface of the catheter 13, a method of using alloy containing precious metal in a metal wire composing the braiding tube 3, a method of mixing a substance with the X-ray impermeability in a resin composing at least one of the braiding tube 3 and the tube 2 made of a resin, etc. However, a method of mixing a substance with the X-ray impermeability in a resin composing at least one of the braiding tube 3 and the tube 2 made of a resin and a method of providing a marker 11 composed of a material having the X-ray impermeability on the external surface or inner surface of the catheter 13 are preferable from the viewpoint of keeping the flexibility of the catheter 13 as high as possible. When the marker 11 is provided, the number of the markers 11 is not limited. One marker may be provided only at the distal end portion of the catheter 13 (FIG. 7) and provided around the side holes 10 (FIG. 8).

The method of mixing a substance with the X-ray impermeability in a resin includes a method of preparing the pellets of a resin preliminarily kneading a substance with the X-ray impermeability and using the pellets, a method of mixing a resin with the substance with the X-ray impermeability at preparing the braiding tube 3 and/or the tube 2 made of a resin, etc. Any method may be used.

The kind of the substance with the X-ray impermeability is not specifically limited and metal compounds such as barium and bismuth and precious metal compounds such as gold and platinum are preferably used, but the oxides of barium, bismuth and the like are preferable in particular from the viewpoint of adaptability to the above-mentioned preparation methods.

The content of the substance with the X-ray impermeability is preferably as high as possible within a range not greatly damaging the physical properties of the resin and capable of molding processing. When the above-mentioned oxides of barium and bismuth are used, at least 30% by weight is preferable.

It is preferable to carry out hydrophilic coating on the external surface of the catheter 13 in order to improve operability at introducing the catheter 13 into the coronary sinus and to reduce the dangerousness of damage accompanied by introduction. The reduction of frictional resistance at introducing it into biolumen can be carried out by the hydrophilic coating. The kind of the coating material is not limited and can be selected matching with the physical properties of the braiding tube 3 and the tube 2 used. As one example, hydrophilic polymers such as a poly(2-hydroxyethyl methacrylate), a polyacryl amide and a polyvinyl pyrrolidone can be used. The frictional resistance may be adjusted to be gradually increased and decreased by adjusting the kind and coating thickness of coating materials to the length direction of the catheter 13.

The catheter is occasionally induced by the guide wire 12 in order to be more easily introduced into the coronary sinus. In this case, the catheter is introduced into the body in a state in which the guide wire 12 is arranged in the inside of the catheter 13 in like manner as that the guide catheter is engaged with the inlet portion of the coronary artery at PCI. A lumen (guide wire lumen) inserting the guide wire 12 independent from the lumen 6 for extraction may be provided in the inside of the catheter, but when the guide wire lumen is provided without changing the equivalent diameter of the lumen 6 for extraction for keeping the extracting amount, it is not preferable because the outer diameter of the catheter increases inevitably. Accordingly, the lumen 6 for extraction is preferably used as the guide wire lumen.

Figure 9:
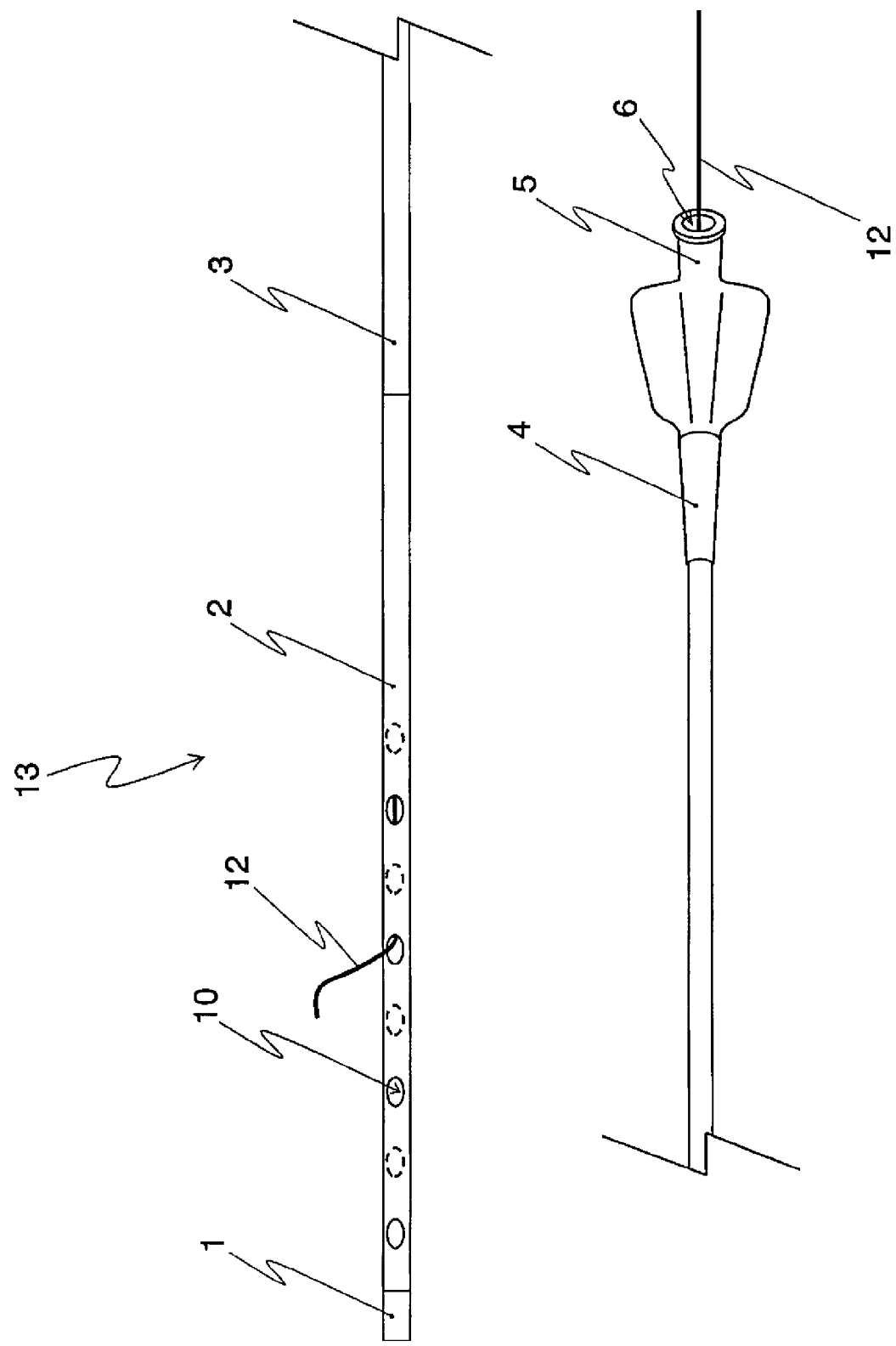
FIG. 9 is a schematic view showing a state in which a guide wire bursts forth from the side holes of the catheter for extraction of the present invention.
Figure 22:
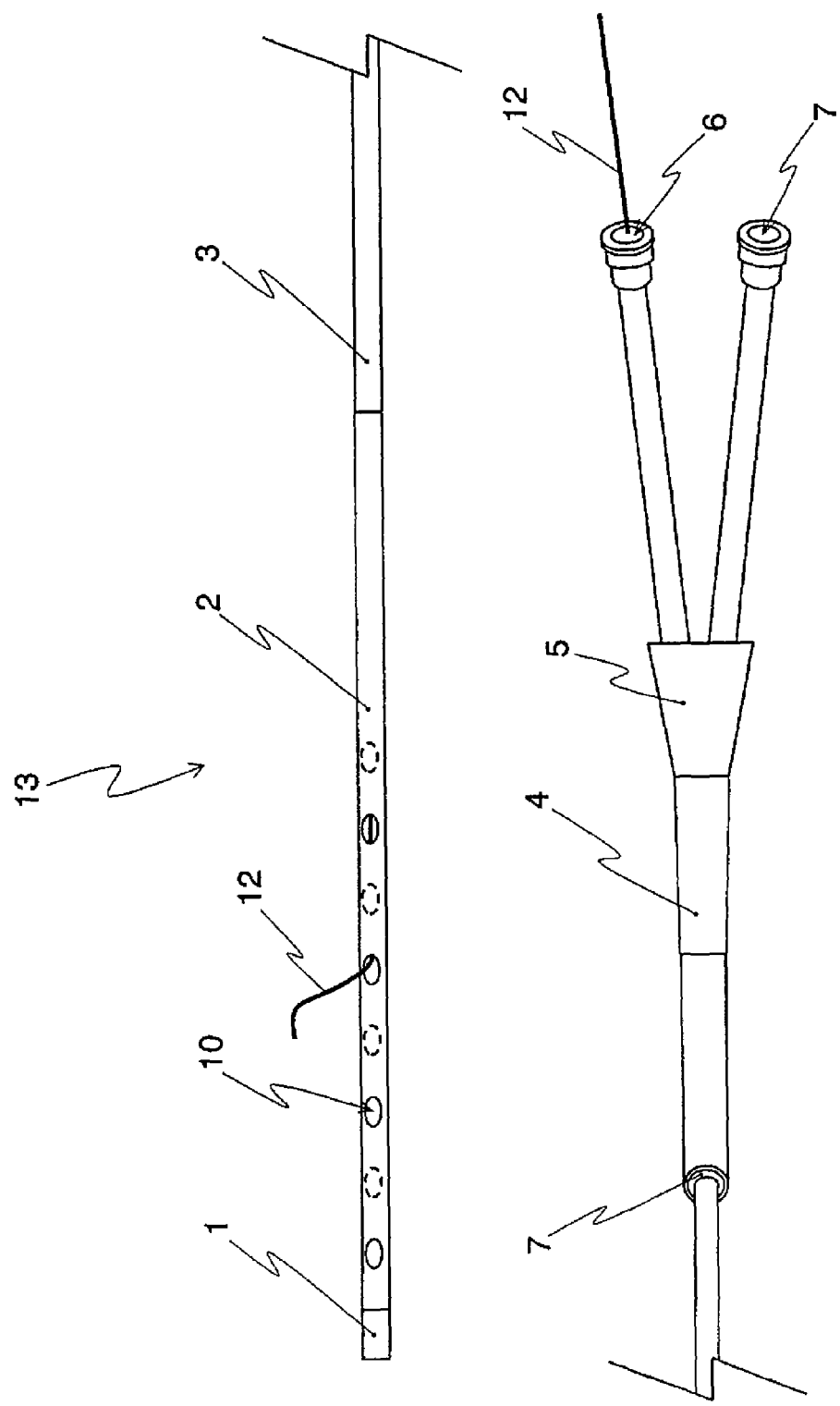
FIG. 22 is a schematic view showing a state in which a guide wire bursts forth from the side holes of the catheter for the extracorporeal circulation of the present invention.

When the guide wire 12 is inserted from the hub 5 of the catheter 13 related to the present invention, in particular, when the edge of the guide wire 12 has a J-type curve, the edge of the guide wire 12 is protruded from the side holes 10 provided at the catheter 13 as shown in FIGS. 9 and 22; therefore induction by the guide wire 12 cannot be easily carried out. Further, when the guide wire 12 is inserted into the catheter 13 introduced into the biolumen once and the edge of the guide wire 12 is protruded from the side holes 10, the guide wire 12 must be adjusted under X-ray fluoroscopic control so that the edge of the guide wire 12 is protruded from the edge of the catheter. It takes very long time to carry out the adjustment under X-ray fluoroscopic control, and the stress of an operator is not only enhanced but also burden to a patient is enlarged. Further, when operation is continued under X-ray fluoroscopic control without feeling that the guide wire 12 is protruded from the side holes 10, there is possibility of plasmotomy of the catheter 13 caused by the break of the side holes 10; therefore it is dangerous.

Figure 11:
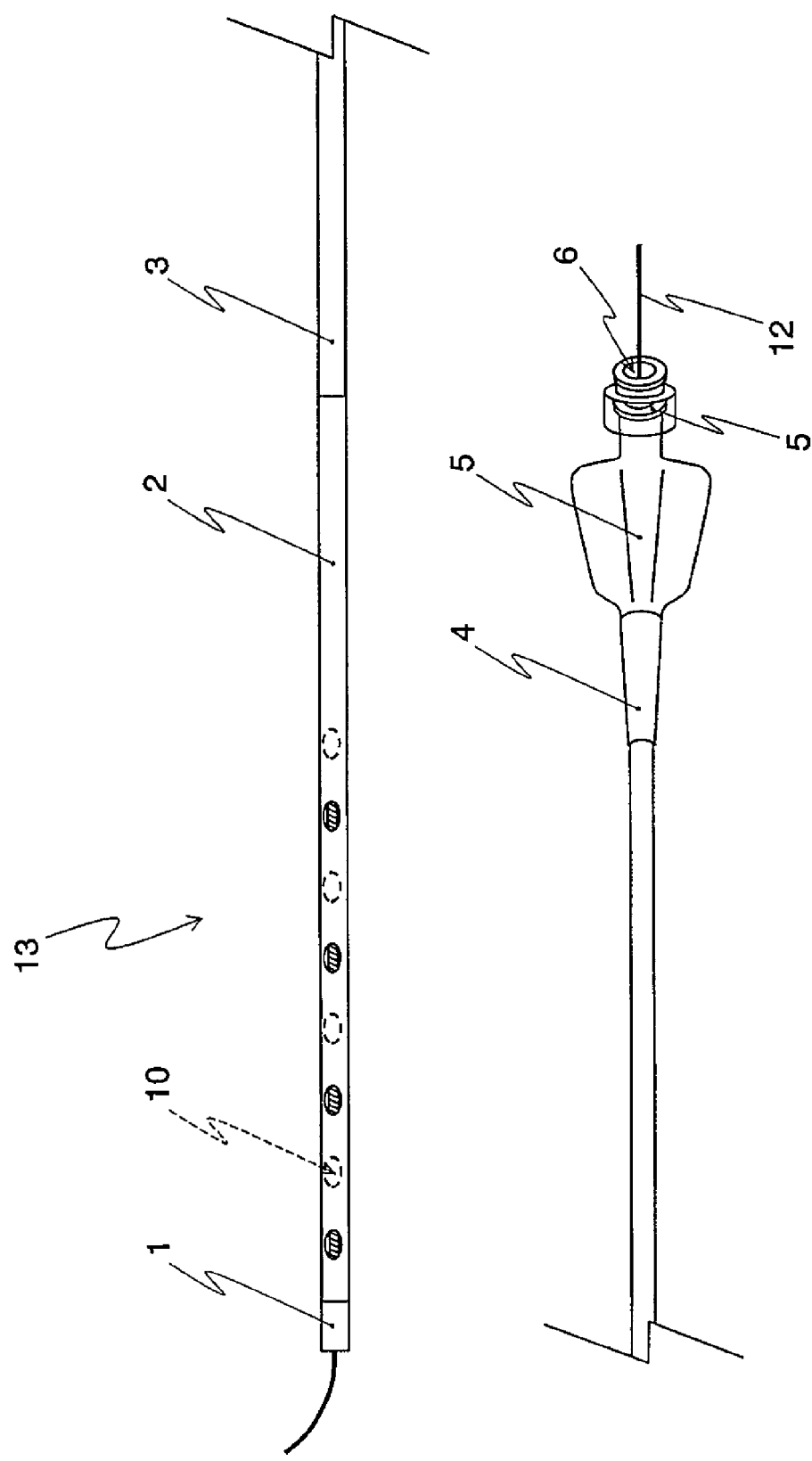
FIG. 11 is a schematic view showing a state in which a guide wire is inserted in the catheter for extraction of the present invention equipped with a subcatheter.
Figure 12:
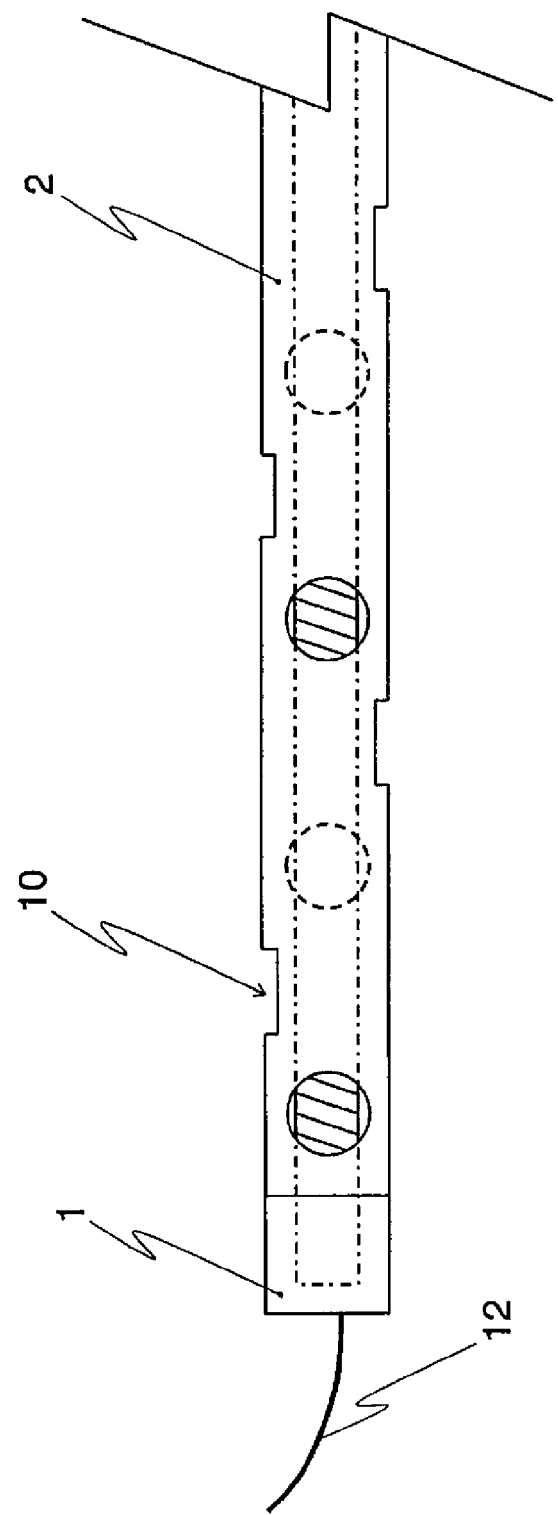
FIG. 12 is a magnified view at the distal end side of the catheter for extraction shown in FIG. 11 and the catheter for extracorporeal circulation shown in FIG. 23.
Figure 13:
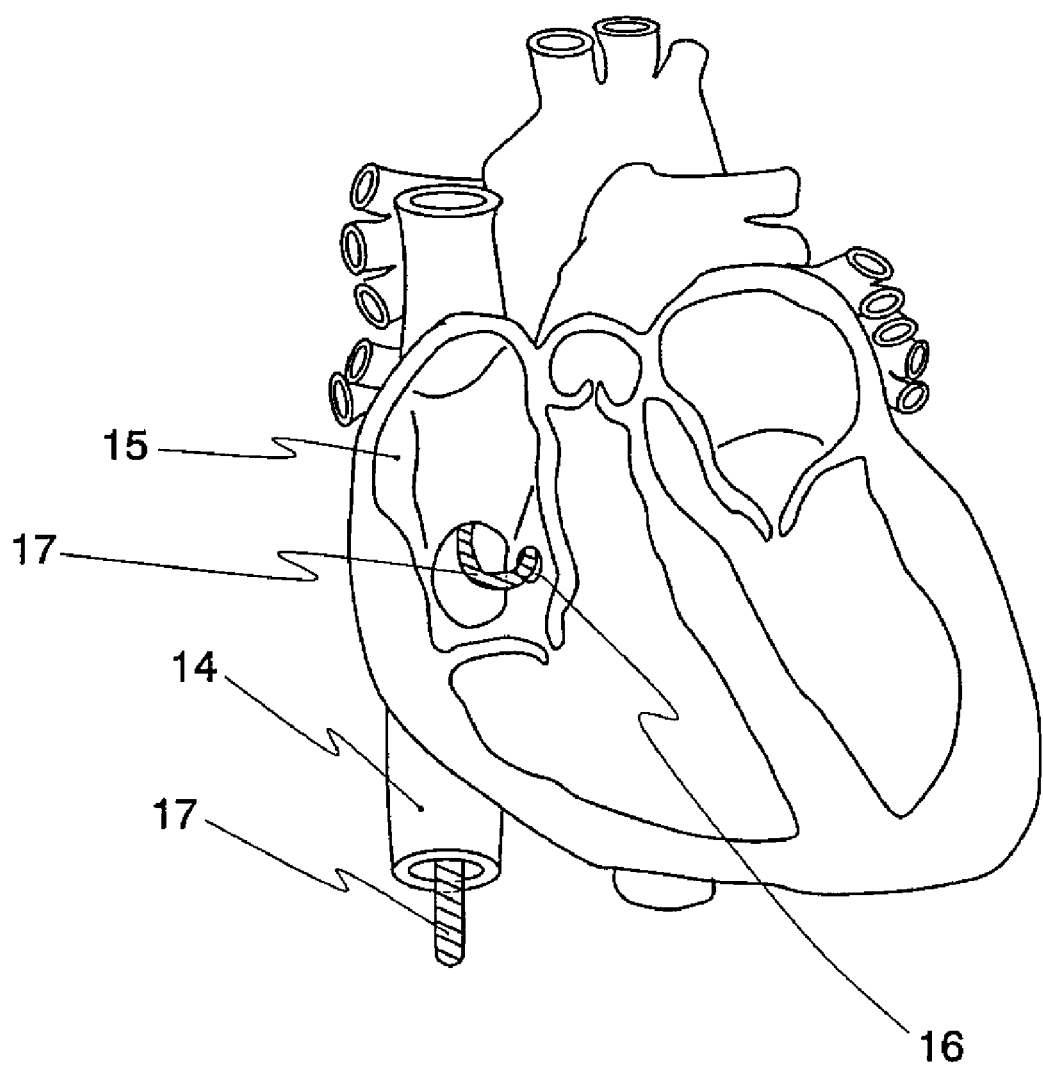
FIG. 13 is a sectional view of the typical heart.
Figure 23:
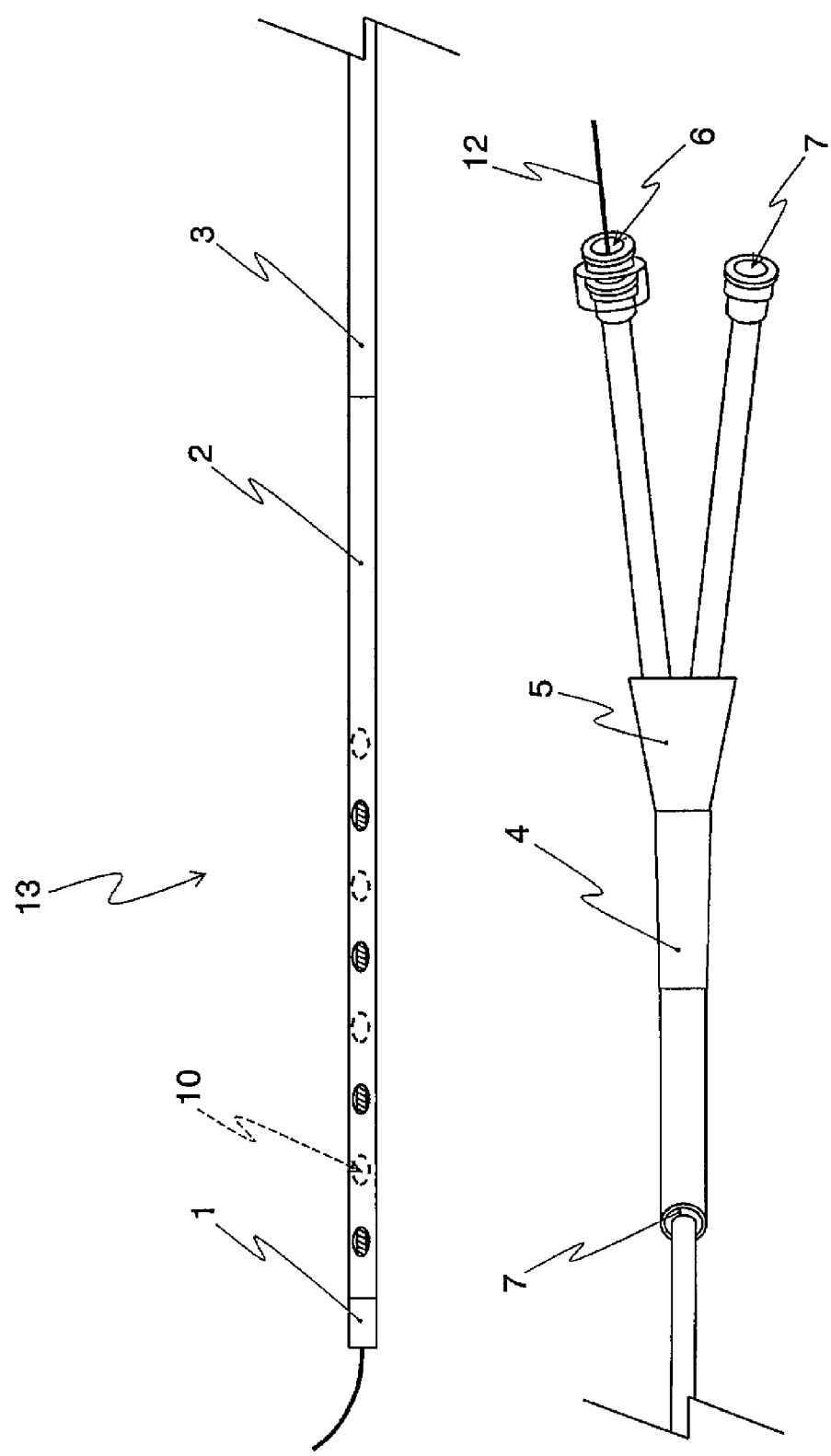
FIG. 23 is a schematic view showing a state in which a guide wire is inserted in the catheter for extracorporeal circulation of the present invention equipped with a subcatheter.

As shown in FIGS. 11 and 23, it is preferable from the above description to have a subcatheter detachably installed in the lumen 6 for extraction of the catheter related to the present invention. As shown in FIG. 12, phenomenon that the guide wire 12 is protruded from the side holes 10 of the catheter 13 can be prevented by using the lumen of the subcatheter as the guide wire lumen. Although the minimum sectional area to the circumferential direction of the blood extracting lumen 6 is decreased by arranging the subcatheter in the blood extracting lumen 6, the extracting amount can be maintained by removing the subcatheter at extraction of the blood because the subcatheter is detachably provided. When the catheter is required again to be operated together with the guide wire 12 after removing the subcatheter, the guide wire 12 may be inserted after the subcatheter is arranged in the blood extracting lumen 6; therefore the operation can be safely carried out.

Figure 10:
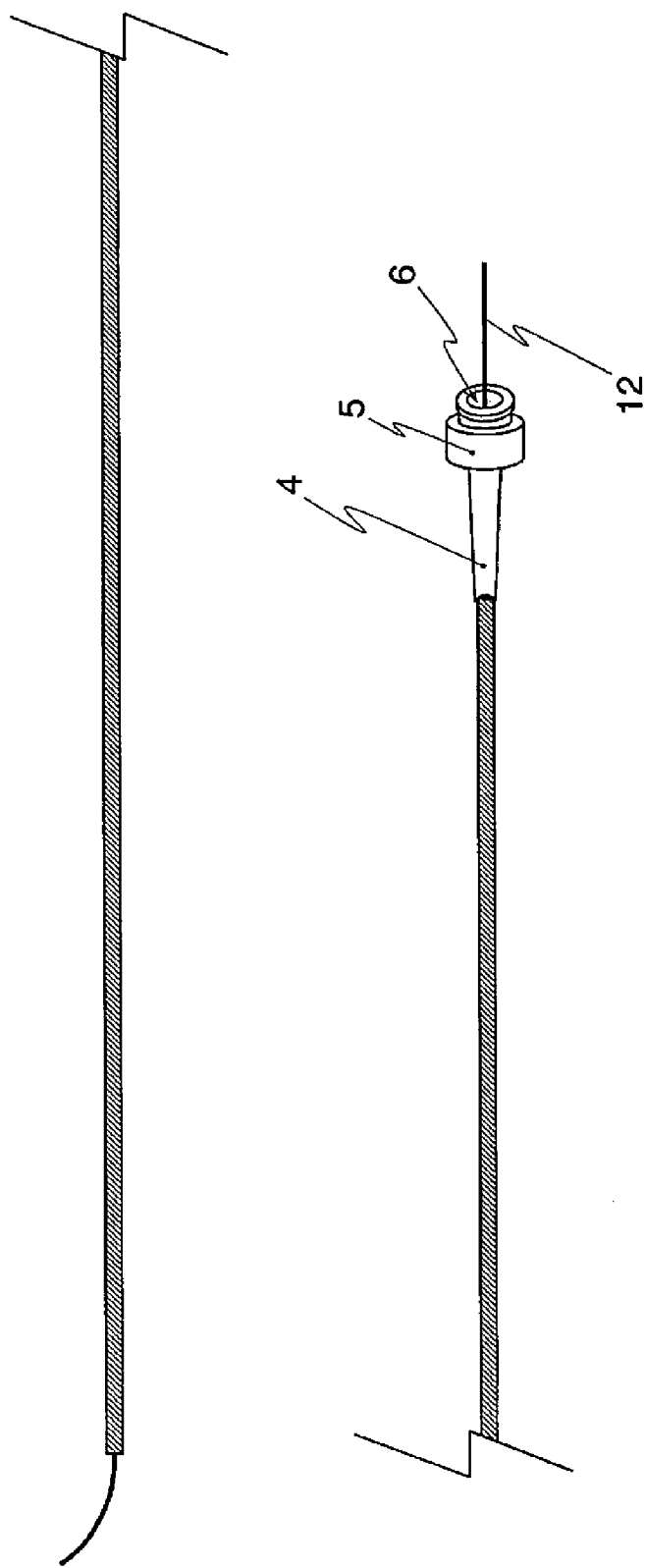
FIG. 10 is a schematic view of the subcatheter of the present invention.

The subcatheter shown in FIG. 10 is composed of a flexible tube member and preferably equipped with a hub 5 at the proximal end portion. Even if a bent shape is provided for the catheter 13 for extracorporeal circulation, it can be easily detached by composing it with a flexible member. Further, the inside of the subcatheter can be flushed with saline with heparin and the like by providing the hub 5 at the proximal end portion and thrombus formation at use is suppressed to be able to be safely used. The connection method of the subcatheter with the catheter 13 for extracorporeal circulation is not limited, but as an example, it can be detachably connected with the proximal end (negative type lure) of the hub 5 provided at the proximal end of the catheter 13 for extracorporeal circulation, by designing the distal end of the hub 5 as positive type lure, as shown in FIGS. 10, 11 and 23.

The tube member is preferably composed of the tube 2 made of a resin and the resin is preferably either of a high density polyethylene and a low density polyethylene, or either of a polytetrafluoroethylene (PTFE), a tetrafluoroethylene-perfluoroalkyl vinyl ether copolymer (PFA), a tetrafluoroethylene-hexafluoropropylene copolymer (FEP), a tetrafluoroethylene-ethylene copolymer (ETFE), a polyvinylidene fluoride (PVDF) and a polychlorotrifluoroethylene (PCTFE) or a polyamide elastomer. Not only frictional resistance at detaching the subcatheter in the catheter 13 for extracorporeal circulation, but also frictional resistance between the subcatheter and the guide wire 12 can be reduced by using either of the above-mentioned materials and good operability can be realized.

The subcatheter has also the X-ray impermeability in like manner as the catheter 13. As the method of providing the X-ray impermeability, a method of providing the marker 11 composed of a material having the X-ray impermeability on the external surface or internal surface of the subcatheter and a method of mixing a substance having the X-ray impermeability with the resin composing the subcatheter are preferable from the viewpoint of keeping the flexibility of the subcatheter as high as possible and realizing the high X-ray impermeability.

The material composing the marker 11 is not specifically limited and metal compounds such as barium and bismuth and precious metal compounds such as gold and platinum are preferably used.

The method of mixing a substance with the X-ray impermeability in the resin includes a method of preparing the pellets of a resin preliminarily kneading a substance with the X-ray impermeability and using the pellets, a method of mixing the resin with the substance with the X-ray impermeability at preparing the tube 2 made of a resin, etc. Any method may be used.

The kind of the substance with the X-ray impermeability is not specifically limited and metal compounds such as barium and bismuth and precious metal compounds such as gold and platinum are preferably used, but the oxides of barium, bismuth and the like are preferable in particular from the viewpoint of adaptability to the above-mentioned preparation methods. Further, the content is preferably as high as possible within a range not greatly damaging the physical properties of the resin and capable of molding processing. When the above-mentioned oxides of barium and bismuth are used, at least 30% by weight is preferable.

When the subcatheter is installed in the catheter 13 for extracorporeal circulation, the relative position of the mutual catheters does not limit the effect of the present invention.

Namely, the distal end of the subcatheter may be arranged at the distal end side than the distal end of the catheter 13 and may be arranged at the proximal end side than the distal end of the catheter 13. It is preferable that the tip 1 is provided at the most distal end portion of the catheter 13 in order to prevent the damage of the coronary sinus in which the catheter 13 is arranged, in any arrangement state.

Further, when the distal end of the subcatheter is arranged at the distal end side than the distal end of the catheter 13, it is preferable that the tip 1 is provided at the distal end of the subcatheter. Further, when the distal end of the subcatheter is arranged at the proximal end side than the distal end of the catheter 13, it is preferable that the tip 1 is provided at the distal end of the catheter 13. The damage of the coronary sinus is suppressed by providing the tip 1 at a portion positioning at the most distal end in a state in which the subcatheter and the catheter 13 are installed.

Since the tip 1 is for suppressing the damage of the coronary sinus as described above, it is preferably flexible. Namely, the tip 1 is formed by a resin, and the Shore hardness of the resin is preferably an elastomer of at least 25D and at most 40D or the blend of the elastomers. When only an elastomer with a Shore hardness of less than 25D is used, it is not preferable because strength is difficult to be kept. When only an elastomer with more than 40D is used, it is not preferable because the flexibility is lowered. The elastomer may be blended at an arbitrary ratio for realizing objective strength and flexibility. It is unnecessary to use the same resin over the full length of the tip 1 and gradient may be provided for physical properties to the length direction of the tip 1 using a plurality of resins.

Since the tip 1 is the most distal end in a state in which the subcatheter and the catheter 13 are installed, it is necessary to grasp an accurate position under X-ray fluoroscopic control. Consequently, it is preferable that the substance with the X-ray impermeability is mixed with the resin composing the tip 1.

The method of mixing the substance with the X-ray impermeability with the resin includes a method of preparing the pellets of a resin preliminarily kneading a substance with the X-ray impermeability and using the pellets, a method of mixing the resin with the substance with the X-ray impermeability at preparing the tube 2 made of a resin, etc. Any method may be used.

The kind of the substance with the X-ray impermeability is not specifically limited and metal compounds such as barium and bismuth and precious metal compounds such as gold and platinum are preferably used, but the oxides of barium, bismuth and the like are preferable in particular from the viewpoint of adaptability to the above-mentioned preparation methods. Further, the content is preferably as high as possible within a range not greatly damaging the physical properties of the resin and capable of molding processing. When the above-mentioned oxides of barium and bismuth are used, at least 30% by weight is preferable.

The production process of the subcatheter and the catheter 13 related to the present invention does not limit the effect of the present invention. The typical structure of the catheter for extraction is those shown in FIGS. 1 to 4 and the typical structure of the catheter 13 for extracorporeal circulation is those shown in FIGS. 14, 19 to 21. The tip 1 is connected with the tube 2 made of a resin, the tube 2 made of a resin is connected with the braiding tube 3, the braiding tube 3 is connected with the hub 5, and a strain relief 4 is connected with the connection portion of the braiding tube 3 with the hub 5 in order to prevent such as kink at using the catheter. The typical structure of the subcatheter is as shown in FIG. 10, the tip 1 is connected with the tube 2 made of a resin, the tube 2 made of a resin is connected with the hub 5, and a strain relief 4 is connected with the connection portion of the tube 2 made of a resin with the hub 5 in order to prevent such as kink at using the catheter.

The connection method in the respective connection portions is not specifically limited and methods such as adhesion using an adhesive and heating adhesion can be used.

In case by adhesion, the kind of the adhesive used is not limited and adhesives such as cyano acrylate, urethane, silicone and epoxy can be preferably used. The effect form of the adhesive is not also limited and adhesives such as a two liquid mixing type, a water-absorbing curing type, a heat curing type and a UV curing type can be preferably used. An adhesive having hardness after curing in which the rigidity of a connection site is not changed in a discontinuous manner before and after the connection site is preferably used and the adhesive can be selected considering the material glued such as material quality, dimension, rigidity. Such as heating treatment, polishing treatment may be carried out before and after adhesion for narrowing the diameter of the connection site and in case of a poorly adhesive material, surface treatment such as plasma treatment using oxygen gas may be carried out.

The material quality composing the hub 5 is not specifically limited and an injection moldable general-purpose resin is preferably used. One example includes such as a polycarbonate, a polyamide, a polyurethane, a polysulfone, a polyarylate, a styrene-butadiene copolymer, a polyolefin.

Specific Examples and Comparative Example related to the present invention are illustrated below, but the present invention is not limited to Examples below.

Preparation of Catheter For Extraction And Its Functional Evaluation

EXAMPLE 1

A braiding tube having an outer diameter of 2.05 mm, an inner diameter of 1.85 mm and a length of 900 mm was prepared using a braiding metal that was obtained by processing a metal wire with 0.10 mm×0.03 mm prepared from SUS 304 alloy by one holding and 16 hits. An inner layer was prepared using a polytetrafluoroethylene (POLYFRON F-207; Daikin Industries Ltd.) and an outer layer was prepared by a switching extrusion process using 4 kinds of polyamide elastomers (PEBAX7233SA01 (Shore hardness of 72D), PEBAX6333SA01 (Shore hardness of 63D), PEBAX5533SA01 (Shore hardness of 55D) and PEBAX4033SA01 (Shore hardness of 40D); Elf Atochem Inc.).

A tube having an outer diameter of 3.00 mm, an inner diameter of 2.25 mm and a length of 150 mm was prepared using a polyamide elastomer (PEBAX4033SA01 (Shore hardness of 40D); Elf Atochem Co.) by an extrusion molding. A core material having an outer diameter of 2.20 mm made of SUS304 alloy that was preliminarily shaped was inserted into the inside of the tube. It was heated in an oven at 180° C. for 45 min in a state in which a thermally shrinking tube made of a polyolefin covered it and shaping process as shown in FIG. 2 was carried out thereto to prepare a tube made of a resin. Further, a tip having a length of 5 mm prepared with a polyamide elastomer (PEBAX3533SA01 (Shore hardness of 35D); Elf Atochem Co.) was thermally deposited on the edge of the tube made of a resin.

After the braiding tube was thermally deposited with the tube made of a resin, a strain relief prepared with a polyamide elastomer (PEBAX5533SA01; Elf Atochem Co.) and a hub prepared with a polycarbonate (Makloron 2658; Bayer AG) were glued with a two liquid mixing type urethane adhesive (UR0531, H.B. Fuller Co.) to prepare a catheter for extraction.

D1 in Example 1 is 1.85 mm.

EXAMPLE 2

A braiding tube was prepared in like manner as Example 1 except an outer diameter of 2.95 mm and an inner diameter of 2.75 mm.

A tube made of a resin was prepared in like manner as Example 1 except that a tube was prepared using a polyamide elastomer (PEBAX3533SA01 (Shore hardness of 35D); Elf Atochem Inc.) and two side holes with a diameter of 2.10 mm were provided using excimer laser. The phase difference of the side holes was 180° and distance between the side holes to a length direction was 40 mm. A catheter for extraction was prepared in like manner as Example 1 using the braiding tube and the tube made of a resin obtained.

A tube made of resin having an outer diameter of 2.20 mm, an inner diameter of 1.90 mm and a length of 1050 mm was prepared using a low density polyethylene (LF480M, Japan Polychem Corporation) by extrusion molding and a hub prepared with a polycarbonate (Makloron 2658; Bayer AG) was glued at one end with a two liquid mixing type urethane adhesive (UR0531, H.B. Fuller Inc.) to prepare a subcatheter. Oxygen plasma treatment was carried out before adhesion.

D1 in Example 2 is 2.25 mm and D3 is 2.10 mm.

EXAMPLE 3

A braiding tube was prepared in like manner as Example 1 except an outer diameter of 2.40 mm and an inner diameter of 2.20 mm. A tube made of a resin was prepared in like manner as Example 1 except that a tube was prepared using a polyamide elastomer (PEBAX5533SA01 (Shore hardness of 55D); Elf Atochem Inc.) and two side holes with a diameter of 1.85 mm were provided using excimer laser. The phase difference of the side holes was 180° and distance between the side holes to a length direction was 40 mm. A catheter for extraction was prepared in like manner as Example 1 using the braiding tube and the tube made of a resin obtained.

A subcatheter was prepared in like manner as Example 2 except an outer diameter of 1.80 mm and an inner diameter of 1.50 mm.

D1 in Example 3 is 2.20 mm and D3 is 1.85 mm.

EXAMPLE 4

A catheter for extraction was prepared in like manner as Example 3 except that the number of side holes was 10, the phase difference of the side holes was 90° and distance between the side holes to a length direction was 5 mm.

A subcatheter was prepared in like manner as Example 3.

D1 in Example 4 is 2.20 mm and D3 is 1.85 mm.

COMPARATIVE EXAMPLE

A braiding tube was prepared in like manner as Example 1 except an outer diameter of 1.80 mm and an inner diameter of 1.60 mm. A tube made of a resin was prepared in like manner as Example 1 except that an outer diameter was 2.40 mm, an inner diameter was 1.60 mm and a core material used at a shaping process was an outer diameter of 1.55 mm. A catheter for extraction was prepared in like manner as Example 1 using the braiding tube and the tube made of a resin obtained.

D1 in Comparative Example 1 is 1.60 mm and D3 is 1.60 mm.

(Evaluation)

A sheath introducer of right femoral vein 10 Fr was inserted for an LWD pig having a weight of 58.5 kg under an inhalation anesthesia. The catheter for extraction was deployed into the coronary sinus under X-ray fluoroscopic control. A guide wire with 0.035" was used in combination, the subcatheter was deployed into a state in which it was arranged in the catheter for extraction from Example 2 to Example 4, and the subcatheter was removed after the deployment.

Extraction of the blood was carried out using a blood drawing pump in a state in which an extension tube having a length of 1000 mm was connected with the hub of the catheter for extraction and extracting pressure and extracting amount were measured.

(Result)

Any one of Examples 1 to 4 related to the present invention and Comparative Example could be deployed into the coronary sinus. Further, in Examples 2 to 4, the guide wire was not protruded from the side holes of the catheter for extraction according to the effect of the subcatheter and operability was good.

The extraction of the blood could be carried out at a speed of 100 mL/min at an extracting pressure of −80 mmHg in Example 1, −18 mmHg in Example 2, −33 mmHg in Example 3 and −30 mmHg in Example 4. A condition that extracting amount is at least 80 mL/min was satisfied at an extracting pressure of at least −100 mmHg that is preferable condition for extracting the blood containing a contrast medium and hydrating the blood from which the contrast medium was removed by a blood purifying method such as adsorption, in the body.

On the other hand, in Comparative Example, only the extracting amount of about 60 mL/min was obtained at the extracting pressure range of at least −100 mmHg and it was considered that applicability to a system of extracting the blood containing a contrast medium and hydrating the blood from which the contrast medium was removed by a blood purifying method such as adsorption, in the body was difficult.

Preparation of Catheter For Extracorporeal Circulation And Its Functional Evaluation

EXAMPLE 5

A braiding tube having an outer diameter of 2.69 mm, an inner diameter of 2.29 mm and a length of 900 mm was prepared using a braiding metal that was obtained by processing a metal wire with 0.10 mm×0.03 mm prepared from SUS 304 alloy by one holding and 16 hits. An inner layer was prepared using a polytetrafluoroethylene (POLYFRON F-207; Daikin Industries Ltd.) and an outer layer was prepared by a switching extrusion process using 4 kinds of polyamide elastomers (PEBAX7233SA01 (Shore hardness of 72D), PEBAX6333SA01 (Shore hardness of 63D), PEBAX5533SA01 (Shore hardness of 55D) and PEBAX4033SA01 (Shore hardness of 40D); Elf Atochem Inc.) in which barium sulfate was contained by 40% by weight by a biaxial kneading extrusion process.

A tube having an outer diameter of 3.00 mm, an inner diameter of 2.25 mm and a length of 150 mm was prepared using a polyamide elastomer (PEBAX4033SA01 (Shore hardness of 40D); Elf Atochem Inc.) in which barium sulfate was contained by 40% by weight by a biaxial kneading extrusion process. A core material having an outer diameter of 2.20 mm made of SUS304 alloy that was preliminarily shaped was inserted into the inside of the tube. It was heated in an oven at 180° C. for 45 min in a state in which a thermally shrinking tube made of a polyolefin covered it and shaping process as shown in FIG. 19 was carried out thereto to prepare a tube made of a resin. Further, a tip having a length of 5 mm prepared with a polyamide elastomer (PEBAX3533SA01 (Shore hardness of 35D); Elf Atochem Inc.) in which barium sulfate was contained by 40% by weight by a biaxial kneading extrusion process was thermally deposited on the edge of the tube made of a resin.

The braiding tube and the tube made of a resin were connected by thermal deposition to prepare a shaft. A braiding tube having an outer diameter of 4.40 mm, an inner diameter of 4.40 mm and a length of 100 mm was prepared using a braiding metal that was obtained by processing a metal wire with 0.10 mm×0.03 mm prepared from SUS 304 alloy by one holding and 16 hits. An inner layer was prepared using a polytetrafluoroethylene (POLYFRON F-207; Daikin Industries Ltd.) and an outer layer was prepared by a switching extrusion process using a polyamide elastomer (PEBAX7233SA01 (Shore hardness of 72D); Elf Atochem Inc.) in which barium sulfate was contained by 40% by weight by a biaxial kneading extrusion process, to prepare an outside tube. The outside tube was arranged at the outside of the shaft in a double tube shape and the distal portion of the outside tube was protruded by 10 mm from the shaft distal portion with which the braiding tube was connected. The both distal portions of the outside tube and the braiding tube were glued with a two liquid mixing type urethane adhesive (UR0531, H.B. Fuller Inc.) to prepare a sectional structure shown in FIG. 16.

A strain relief prepared with a polyamide elastomer (PEBAX5533SA01; Elf Atochem Inc.) and a hub prepared with a polycarbonate (Makloron 2658; Bayer AG) were glued at the edge of the braiding tube that was protrude by 10 mm from the shaft distal portion with a two liquid mixing type urethane adhesive (UR0531, H.B. Fuller Inc.) to prepare a catheter for extracorporeal circulation.

D1 in Example 5 is 2.25 mm and D2 is 1.31 mm.

EXAMPLE 6

A catheter for extracorporeal circulation was prepared in like manner as Example 5 except that two circular side holes with a diameter of 1.85 mm were provided using excimer laser and the full length of the outside tube was 300 mm. The phase difference of the side holes was 180° and distance between the side holes to a length direction was 40 mm. The catheter for extracorporeal circulation was prepared in like manner as Example 5 using the braiding tube and the tube made of a resin obtained.

A tube made of resin having an outer diameter of 1.60 mm, an inner diameter of 1.10 mm and a length of 1050 mm was prepared using a low density polyethylene (LF480M, Japan Polychem Corporation) by extrusion molding and a hub prepared with a polycarbonate (Makloron 2658; Bayer AG) was glued at one end with a two liquid mixing type urethane adhesive (UR0531, H.B. Fuller Inc.) to prepare a subcatheter. Oxygen plasma treatment was carried out before adhesion.

D1 in Example 6 is 2.25 mm, D2 is 1.31 mm and D3 is 1.85 mm.

EXAMPLE 7

The outer diameter of the edge tube was 2.60 mm, an inner diameter was 1.80 mm and the outer diameter of a core material used for shaping was 1.75 mm. A catheter for extracorporeal circulation was prepared in like manner as Example 6 except that the diameter of side holes was 1.80 mm. A subcatheter was prepared in like manner as Example 6.

D1 in Example 7 is 1.80 mm, D2 is 1.31 mm and D3 is 1.80 mm.

EXAMPLE 8

The number of side holes provided at the edge tube was 10, phase difference was 90° and distance between the side holes to a length direction was 5 mm. A catheter for extracorporeal circulation was prepared in like manner as Example 6 except that the dimension of the outside tube was set as an outer diameter of 5.00 mm, an inner diameter of 4.65 mm and a length of 500 mm. A subcatheter was prepared in like manner as Example 6.

D1 in Example 8 is 2.25, D2 is 1.96 mm and D3 is 1.85 mm.

EXAMPLE 9

A catheter for extracorporeal circulation was prepared in like manner as Example 6 except that side holes with a diameter of 1.30 mm was provided and further, the dimension of the outside tube was an outer diameter of 4.00 mm, an inner diameter of 3.60 mm and a length of 300 mm. A subcatheter was prepared in like manner as Example 6.

D1 in Example 9 is 1.80 mm, D2 is 0.91 mm and D3 is 1.30 mm.

(Evaluation)

A sheath introducer of right femoral vein 15 Fr was inserted for an LWD pig having a weight of 57.7 kg under inhalation anesthesia. The catheter for extraction was deployed into the coronary sinus under X-ray fluoroscopic control. A guide wire with 0.035" was also used in any examples. The subcatheter was deployed into a state in which the subcatheter was in combination with the catheter for extracorporeal circulation from Example 6 to Example 8 and Example 9, and the subcatheter was removed after the deployment.

An extension tube having a length of 500 mm was respectively connected with the blood extracting lumen and the blood return lumen of the catheter for extracorporeal circulation and the extraction and return of the blood was carried out using an extracorporeal circulation device DX21 (Kaneka Corporation).

(Result)

Any one of Examples 5 to 8 and Example 9 related to the present invention could be deployed into the coronary sinus. Further, in Examples 6 to 8 and Example 9, the guide wire was not protruded from the side holes of the catheter for extraction according to the effect of the subcatheter and operability was good.

The extraction of the blood at 80 mL/min could be carried out in any one of Examples 5 to 8 and hydration could be carried out without the increase of extreme returning pressure. Extracting pressure was −85 mmHg in Example 5, −86 mmHg in Example 6, −95 mmHg in Example 7 and −83 mmHg in Example 8. Further, the returning pressure was 50 mmHg in Example 5, 140 mmHg in Example 6, 137 mmHg in Example 7 and 46 mmHg in Example 8. Hemolysis was not confirmed during extracorporeal circulation. The extraction and return could be carried out without providing a blood access for returning the blood extracted, by using the catheter for extracorporeal circulation related to the present invention.

On the other hand, the returning pressure was extremely increased in Example 9 and circulation at 80 mmL/min could not be carried out. Even if the returning pressure was 200 mmHg, extraction speed was about 30 mL/min, it was considered that Examples 5 to 8 were more preferable than Example 9 from the viewpoint of applicability to a system of extracting the blood containing a contrast medium and returning the blood from which the contrast medium was removed by a blood purifying method such as adsorption, in the body.

INDUSTRIAL APPLICABILITY

According to the present invention, the blood flowing in the coronary sinus from the coronary artery through the coronary vein can be efficiently extracted externally. Drugs such as a contrast medium administrated in the coronary artery can be removed by blood purification such as dialysis and adsorption in case of the catheter for extraction, and can be removed by an extracorporeal circulation therapy such as adsorption and filtration in case of the catheters for extracorporeal circulation. As a result, diseases such as kidney functional disorder such as contrast induced nephropathy is effectively suppressed. Further, since the use feeling of the catheter related to the present invention is same as that of catheters used in conventional PCI, the extracorporeal extraction operation of the blood can be carried out without accompanying the excessive extension of surgery time. Further, it is unnecessary to separately provide a blood access for returning the blood extracted; therefore the burden to a patient can be reduced.

The invention claimed is:

1. A method of actuating a catheter for extracorporeal circulation, wherein the catheter has distal end and proximal end, the catheter has blood extracting lumen extending from the distal end to the proximal end and blood return lumen extending from the proximal end of the catheter to the fixed length distal end, the blood is extracted from the distal end of the blood extracting lumen arranged in the coronary sinus of patient's heart and the blood is returned from the blood extracting lumen arranged in the body of a patient into the body of the patient.

2. The method of claim 1, further equipped with that when the minimum sectional area to the circumferential direction of the blood extracting lumen of the catheter for extracorporeal circulation is referred to as S1 and an immersion side length is referred to as L1, an equivalent diameter D1 satisfies the formula defined by D1=(4×S1)/L1 and the equivalent diameter D1 is at least 1.80 mm, and when the minimum sectional area to the circumferential direction of the blood return lumen is referred to as S2 and the immersion side length is referred to as L2, an equivalent diameter D2 satisfies the formula defined by D2=(4×S2)/L2 and the equivalent diameter D2 is at least 1.30 mm and at most 2.00 mm.

* * * * *